US009193770B2

(12) United States Patent
Gally et al.

(10) Patent No.: US 9,193,770 B2
(45) Date of Patent: Nov. 24, 2015

(54) IMMUNOGENIC COMPOSITIONS CONTAINING *ESCHERICHIA COLI* H7 FLAGELLA AND METHODS OF USE THEREOF

(75) Inventors: David Gally, Edinburgh (GB); Tom Nathan McNeilly, Midlothian (GB); David George Emslie Smith, Midlothian (GB); Chris Low, Midlothian (GB); Arvind Kumar Mahajan, Edinburgh (GB); Stuart W. Naylor, Edinburgh (GB)

(73) Assignees: THE UNIVERSITY COURT OF THE UNIVERSITY OF EDINBURGH, Edinburgh (GB); MOREDUN RESEARCH INSTITUTE, Penicuik (GB); THE SCOTTISH AGRICULTURAL COLLEGE, Edinburgh (GB)

( * ) Notice: Subject to any disclaimer, the term of this patent is extended or adjusted under 35 U.S.C. 154(b) by 1590 days.

(21) Appl. No.: 12/738,627

(22) PCT Filed: Oct. 17, 2008

(86) PCT No.: PCT/GB2008/003515
§ 371 (c)(1),
(2), (4) Date: Sep. 1, 2010

(87) PCT Pub. No.: WO2009/050474
PCT Pub. Date: Apr. 23, 2009

(65) Prior Publication Data
US 2011/0008379 A1     Jan. 13, 2011

(30) Foreign Application Priority Data
Oct. 17, 2007  (GB) .................... 0720250.0

(51) Int. Cl.
*A61K 39/00*  (2006.01)
*C07K 14/245* (2006.01)
*A61K 39/108* (2006.01)
*C07K 16/12*  (2006.01)

(52) U.S. Cl.
CPC .......... *C07K 14/245* (2013.01); *A61K 39/0258* (2013.01); *C07K 16/1232* (2013.01); *A61K 39/00* (2013.01); *A61K 2039/552* (2013.01); *A61K 2039/55555* (2013.01); *A61K 2039/55577* (2013.01); *A61K 2039/57* (2013.01); *C07K 2319/00* (2013.01)

(58) Field of Classification Search
None
See application file for complete search history.

(56) References Cited

U.S. PATENT DOCUMENTS

| 7,125,661 | B1 * | 10/2006 | Reeves et al. ................. 435/6.13 |
| 8,119,147 | B2 * | 2/2012 | Emery et al. ................. 424/258.1 |
| 8,173,130 | B2 * | 5/2012 | Salzman et al. ........... 424/150.1 |
| 8,236,327 | B2 * | 8/2012 | Rhee et al. ................. 424/261.1 |
| 8,263,078 | B2 * | 9/2012 | Rachamim et al. ........ 424/142.1 |
| 8,337,864 | B2 * | 12/2012 | Rhee et al. ................. 424/261.1 |
| 8,486,408 | B2 * | 7/2013 | Hossain et al. ........... 424/172.1 |
| 8,647,642 | B2 * | 2/2014 | Bermudes .................. 424/258.1 |
| 2007/0128183 | A1 * | 6/2007 | Meinke et al. ............. 424/130.1 |
| 2009/0191208 | A1 * | 7/2009 | Salzman et al. ........... 424/139.1 |
| 2009/0208506 | A1 * | 8/2009 | Rachamim et al. ........ 424/139.1 |
| 2010/0239583 | A1 * | 9/2010 | Murthy et al. ............. 424/136.1 |
| 2011/0008379 | A1 * | 1/2011 | Gally et al. ................. 424/190.1 |
| 2013/0150286 | A1 * | 6/2013 | Sirard et al. ................... 514/2.6 |

FOREIGN PATENT DOCUMENTS

| WO | WO 99/61458 | A1 * | 12/1999 |
| WO | WO 2005/103073 | A2 * | 11/2005 |
| WO | WO 2006/069292 | A2 * | 6/2006 |
| WO | WO 2009/033009 | A2 * | 3/2009 |
| WO | WO 2009/033013 | A1 * | 3/2009 |
| WO | WO 2009/050474 | A1 * | 4/2009 |
| WO | WO 2010/040096 | A2 * | 4/2010 |
| WO | WO 2011/151491 | A1 * | 12/2011 |
| WO | WO 2014/053996 | A2 * | 4/2014 |

OTHER PUBLICATIONS

Amani et al, Vaccine, 2010, 28:6923-6929.*
Babiuk et al, Microbial Pathogenesis 45 (2008) 7-11.*
McNeilly et al, Veterinary Immunology and Immunopathology 118 (2007) 160-167.*
McNeilly et al, Vaccine 28 (2010) 1422-1428.*
McNeilly et al, Vaccine 28 (2010) 1412-1421.*
Zhang et al, Vaccine 29 (2011) 3923-3929.*
Perna et al, Nature, 2001, 409:529-533.*
Wang et al, J. Clin. Microbiol., 2000, 338:1786-1790.*
Naylor et al, Applied and Environmental Microbiology, Jun. 2007, p. 3765-3767 vol. 73, No. 11.*

* cited by examiner

Primary Examiner — Nita M Minnifield
(74) Attorney, Agent, or Firm — Gilberto M. Villacorta; Tianran Yan; Foley & Lardner LLP

(57) ABSTRACT

Immunogenic compositions containing *Escherichia coli* O157:H7 flagella including fusion proteins and methods using the immunogenic compositions are disclosed. Inducing an immune response in an animal to *Escherichia coli* O157:H7 flagella will result in prevention of colonization by *Escherichia coli* O157:H7 in the animal or a reduction in the amount of *Escherichia coli* O157:H7 infecting the animal. The immune composition will prevent or reduce the attachment of *Escherichia coli* O157:H7 to cells within the animal.

13 Claims, 7 Drawing Sheets

```
  1  ATGGCACAAG TCATTAATAC CAACAGCCTC TCGCTGATCA CTCAAAATAA TATCAACAAG
 61  AACCAGTCTG CGCTGTCGAG TTCTATCGAG CGTCTGTCTT CTGGCTTGCG TATTAACAGC
121  GCGAAGGATG ACGCCGCAGG TCAGGCGATT GCTAACCGTT TTACTTCTAA CATTAAAGGC
181  CTGACTCAGG CGGCCCGTAA CGCCAACGAC GGTATTTCTG TTGCGCAGAC CACCGAAGGC
241  GCGCTGTCCG AAATCAACAA CAACTTACAG CGTATTCGTG AACTGACGGT TCAGGCCACT
301  ACAGGGACTA ACTCCGATTC TGACCTGGAC TCCATCCAGG ACGAAATCAA ATCTCGTCTT
361  GATGAAATTG ACCGCGTATC CGGCCAGACC CAGTTCAACG GCGTGAACGT GCTGGCGAAA
421  GACGGTTCAA TGAAAATTCA GGTTGGTGCG AATGACGGCG AAACCATCAC GATCGACCTG
481  AAAAAAATCG ATTCTGATAC TCTGGGTCTG AATGGCTTTA ACGTAAATGG TAAAGGTACT
541  ATTACCAACA AAGCTGCAAC GGTAAGTGAT TTAACTTCTG CTGGCGCGAA GTTAAACACC
601  ACGACAGGTC TTTATGATCT GAAAACCGAA AATACCTTGT TAACTACCGA TGCTGCATTC
661  GATAAATTAG GGAATGGCGA TAAAGTCACA GTTGGCGGCG TAGATTATAC TTACAACGCT
721  AAATCTGGTG ATTTTACTAC CACTAAATCT ACTGCTGGTA CGGGTGTAGA CGCCGCGGCG
781  CAGGCTGCTG ATTCAGCTTC AAAACGTGAT GCGTTAGCTG CCACCCTTCA TGCTGATGTG
841  GGTAAATCTG TTAATGGTTC TTACACCACA AAAGATGGTA CTGTTTCTTT CGAAACGGAT
901  TCAGCAGGTA ATATCACCAT CGGTGGAAGC CAGGCATACG TAGACGATGC AGGCAACTTG
961  ACGACTAACA ACGCTGGTAG CGCAGCTAAA GCTGATATGA AAGCGCTGCT CAAAGCAGCG
1021 AGCGAAGGTA GTGACGGTGC CTCTCTGACA TTCAATGGCA CAGAATATAC CATCGCAAAA
1081 GCAACTCCTG CGACAACCAC TCCAGTAGCT CCGTTAATCC CTGGTGGGAT TACTTATCAG
1141 GCTACAGTGA GTAAAGATGT AGTATTGAGC GAAACCAAAG CGGCTGCCGC GACATCTTCA
1201 ATTACCTTTA ATTCCGGTGT ACTGAGCAAA ACTATTGGGT TTACCGCGGG TGAATCCAGT
1261 GATGCTGCGA AGTCTTATGT GGATGATAAA GGTGGTATCA CTAACGTTGC CGACTATACA
1321 GTCTCTTACA GCGTTAACAA GGATAACGGC TCTGTGACTG TTGCCGGGTA TGCTTCAGCG
1381 ACTGATACCA ATAAAGATTA TGCTCCAGCA ATTGGTACTG CTGTAAATGT GAACTCCGCG
1441 GGTAAAATCA CTACTGAGAC TACCAGTGCT GGTTCTGCAA CGACCAACCC GCTTGCTGCC
1501 CTGGACGACG CAATCAGCTC CATCGACAAA TTCCGTTCTT CCCTGGGTGC TATCCAGAAC
1561 CGTCTGGATT CCGCAGTCAC CAACCTGAAC AACACCACTA CCAACCTGTC CGAAGCGCAG
1621 TCCCGTATTC AGGACGCCGA CTATGCGACC GAAGTGTCCA ACATGTCAAA AGCGCAGATC
1681 ATTCAGCAGG CCGGTAACTC CGTGCTGGCA AAAGCTAACC AGGTACCGCA GCAGGTTCTG
1741 TCTCTGCTGC AGGGTTAA
```

B

MAQVINTNSLSLITQNNINKNQSALSSSIERLSSGLRINSAKDDAAGQAIANRFTSNIKG 60

LTQAARNANDGISVAQTTEGALSEINNNLQRIRELTVQATTGTNSDSDLDSIQDEIKSRL 120

DEIDRVSGQTQFNGVNVLAKDGSMKIQVGANDGETITIDLKKIDSDTLGLNGFNVNGKGT 180

ITNKAATVSDLTSAGAKLNTTTGLYDLKTENTLLTTDAAFDKLGNGDKVTVGGVDYTYNA 240

KSGDFTTTKSTAGTGVDAAAQAADSASKRDALAATLHADVGKSVNGSYTTKDGTVSFETD 300

SAGNITIGGSQAYVDDAGNLTTNNAGSAAKADMKALLKAASEGSDGASLTFNGTEYTIAK 360

ATPATTTPVAPLIPGGITYQATVSKDVVLSETKAAAATSSITFNSGVLSKTIGFTAGESS 420

DAAKSYVDDKGGITNVADYTVSYSVNKDNGSVTVAGYASATDTNKDYAPAIGTAVNVNSA 480

GKITTETTSAGSATTNPLAALDDAISSIDKFRSSLGAIQNRLDSAVTNLNNTTTNLSEAQ 540

SRIQDADYATEVSNMSKAQIIQQAGNSVLAKANQVPQQVLSLLQG 585

☐ H7 flagellin
☐ Antigen
▨ His-tag

FIGURE 9
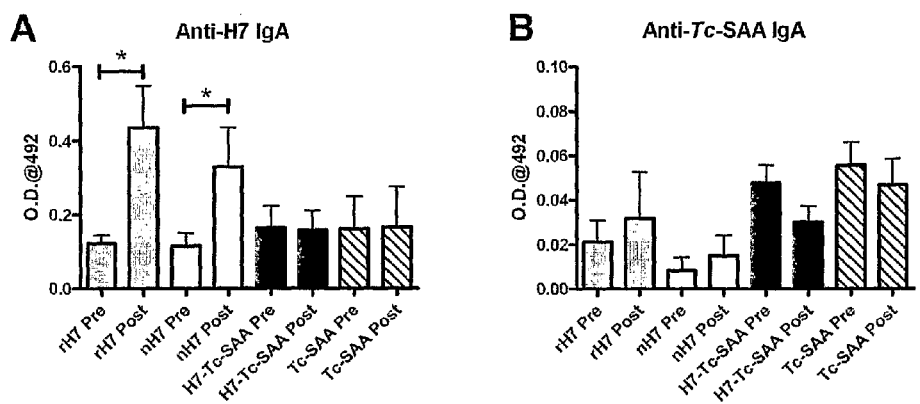
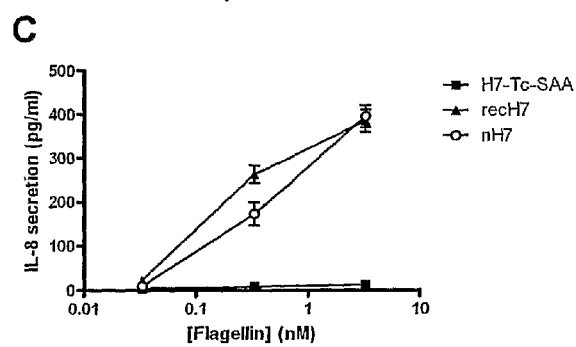
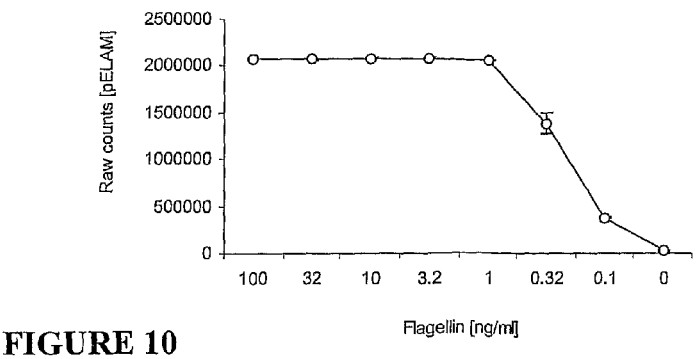
FIGURE 10

SEQUENCE LISTING

<160> NUMBER OF SEQ ID NOS: 6

<210> SEQ ID NO 1
<211> LENGTH: 1758
<212> TYPE: DNA
<213> ORGANISM: Escherichia coli

<400> SEQUENCE: 1

```
atggcacaag tcattaatac caacagcctc tcgctgatca ctcaaaataa tatcaacaag      60
aaccagtctg cgctgtcgag ttctatcgag cgtctgtctt ctggcttgcg tattaacagc     120
gcgaaggatg acgccgcagg tcaggcgatt gctaaccgtt ttacttctaa cattaaaggc     180
ctgactcagg cggcccgtaa cgccaacgac ggtatttctg ttgcgcagac caccgaaggc     240
gcgctgtccg aaatcaacaa caacttacag cgtattcgtg aactgacggt tcaggccact     300
acagggacta actccgattc tgacctggac tccatccagg acgaaatcaa atctcgtctt     360
gatgaaattg accgcgtatc cggccagacc cagttcaacg gcgtgaacgt gctggcgaaa     420
gacggttcaa tgaaaattca ggttggtgcg aatgacggcg aaaccatcac gatcgacctg     480
aaaaaaatcg attctgatac tctgggtctg aatggcttta acgtaaatgg taaaggtact     540
attaccaaca aagctgcaac ggtaagtgat ttaacttctg ctggcgcgaa gttaaacacc     600
acgacaggtc tttatgatct gaaaaccgaa ataccttgt taactaccga tgctgcattc     660
gataaattag ggaatggcga taaagtcaca gttggcggcg tagattatac ttacaacgct     720
aaatctggtg attttactac cactaaatct actgctggta cgggtgtaga cgccgcggcg     780
caggctgctg attcagcttc aaaacgtgat gcgttagctg ccaccctttca tgctgatgtg     840 ggtaaatctg ttaatggttc ttacaccaca aaagatggta ctgtttcttt cgaaacggat     900
tcagcaggta atatcaccat cggtggaagc caggcatacg tagacgatgc aggcaacttg     960
acgactaaca acgctggtag cgcagctaaa gctgatatga aagcgctgct caaagcagcg    1020
agcgaaggta gtgacggtgc ctctctgaca ttcaatggca cagaatatac catcgcaaaa    1080
gcaactcctg cgacaaccac tccagtagct ccgttaatcc ctggtgggat tacttatcag    1140
gctacagtga gtaaagatgt agtattgagc gaaaccaaag cggctgccgc gacatcttca    1200 attacctta attccggtgt actgagcaaa actattgggt ttaccgcggg tgaatccagt    1260
gatgctgcga agtcttatgt ggatgataaa ggtggtatca ctaacgttgc cgactataca    1320
gtctcttaca gcgttaacaa ggataacggc tctgtgactg ttgccgggta tgcttcagcg    1380
actgatacca ataaagatta tgctccagca attggtactg ctgtaaatgt gaactccgcg    1440
ggtaaaatca ctactgagac taccagtgct ggttctgcaa cgaccaaccc gcttgctgcc    1500
ctggacgacg caatcagctc catcgacaaa ttccgttctt ccctgggtgc tatccagaac    1560
cgtctggatt ccgcagtcac caacctgaac aacaccacta ccaacctgtc cgaagcgcag    1620
tcccgtattc aggacgccga ctatgcgacc gaagtgtcca acatgtcgaa agcgcagatc    1680
attcagcagg ccggtaactc cgtgctggca aaagctaacc aggtaccgca gcaggttctg    1740
tctctgctgc agggttaa                                                  1758
```

```
<210> SEQ ID NO 2
<211> LENGTH: 585
<212> TYPE: PRT
<213> ORGANISM: Escherichia coli

<400> SEQUENCE: 2
```

| | | | | | | | | | | | | | | |
|---|---|---|---|---|---|---|---|---|---|---|---|---|---|---|
| Met | Ala | Gln | Val | Ile | Asn | Thr | Asn | Ser | Leu | Ser | Leu | Ile | Thr | Gln | Asn |
| 1 | | | | 5 | | | | | 10 | | | | | 15 | |
| Asn | Ile | Asn | Lys | Asn | Gln | Ser | Ala | Leu | Ser | Ser | Ser | Ile | Glu | Arg | Leu |
| | | | 20 | | | | | 25 | | | | | 30 | | |
| Ser | Ser | Gly | Leu | Arg | Ile | Asn | Ser | Ala | Lys | Asp | Asp | Ala | Ala | Gly | Gln |
| | | 35 | | | | | 40 | | | | | 45 | | | |
| Ala | Ile | Ala | Asn | Arg | Phe | Thr | Ser | Asn | Ile | Lys | Gly | Leu | Thr | Gln | Ala |
| 50 | | | | | 55 | | | | | 60 | | | | | |
| Ala | Arg | Asn | Ala | Asn | Asp | Gly | Ile | Ser | Val | Ala | Gln | Thr | Thr | Glu | Gly |
| 65 | | | | 70 | | | | | 75 | | | | | 80 | |
| Ala | Leu | Ser | Glu | Ile | Asn | Asn | Asn | Leu | Gln | Arg | Ile | Arg | Glu | Leu | Thr |
| | | | | 85 | | | | | 90 | | | | | 95 | |
| Val | Gln | Ala | Thr | Thr | Gly | Thr | Asn | Ser | Asp | Ser | Asp | Leu | Asp | Ser | Ile |
| | | | 100 | | | | | 105 | | | | | 110 | | |
| Gln | Asp | Glu | Ile | Lys | Ser | Arg | Leu | Asp | Glu | Ile | Asp | Arg | Val | Ser | Gly |
| | | 115 | | | | | 120 | | | | | 125 | | | |
| Gln | Thr | Gln | Phe | Asn | Gly | Val | Asn | Val | Leu | Ala | Lys | Asp | Gly | Ser | Met |
| | 130 | | | | | 135 | | | | | 140 | | | | |
| Lys | Ile | Gln | Val | Gly | Ala | Asn | Asp | Gly | Glu | Thr | Ile | Thr | Ile | Asp | Leu |
| 145 | | | | | 150 | | | | | 155 | | | | | 160 |
| Lys | Lys | Ile | Asp | Ser | Asp | Thr | Leu | Gly | Leu | Asn | Gly | Phe | Asn | Val | Asn |
| | | | | 165 | | | | | 170 | | | | | 175 | |
| Gly | Lys | Gly | Thr | Ile | Thr | Asn | Lys | Ala | Ala | Thr | Val | Ser | Asp | Leu | Thr |
| | | | 180 | | | | | 185 | | | | | 190 | | |
| Ser | Ala | Gly | Ala | Lys | Leu | Asn | Thr | Thr | Thr | Gly | Leu | Tyr | Asp | Leu | Lys |
| | | 195 | | | | | 200 | | | | | 205 | | | |
| Thr | Glu | Asn | Thr | Leu | Leu | Thr | Thr | Asp | Ala | Ala | Phe | Asp | Lys | Leu | Gly |
| | 210 | | | | | 215 | | | | | 220 | | | | |
| Asn | Gly | Asp | Lys | Val | Thr | Val | Gly | Gly | Val | Asp | Tyr | Thr | Tyr | Asn | Ala |
| 225 | | | | | 230 | | | | | 235 | | | | | 240 |
| Lys | Ser | Gly | Asp | Phe | Thr | Thr | Lys | Ser | Thr | Ala | Gly | Thr | Gly | Val |
| | | | | 245 | | | | | 250 | | | | | 255 |
| Asp | Ala | Ala | Ala | Gln | Ala | Ala | Asp | Ser | Ala | Ser | Lys | Arg | Asp | Ala | Leu |
| | | | 260 | | | | | 265 | | | | | 270 | | |
| Ala | Ala | Thr | Leu | His | Ala | Asp | Val | Gly | Lys | Ser | Val | Asn | Gly | Ser | Tyr |
| | | 275 | | | | | 280 | | | | | 285 | | | |
| Thr | Thr | Lys | Asp | Gly | Thr | Val | Ser | Phe | Glu | Thr | Asp | Ser | Ala | Gly | Asn |
| | 290 | | | | | 295 | | | | | 300 | | | | |
| Ile | Thr | Ile | Gly | Gly | Ser | Gln | Ala | Tyr | Val | Asp | Asp | Ala | Gly | Asn | Leu |
| 305 | | | | | 310 | | | | | 315 | | | | | 320 |
| Thr | Thr | Asn | Asn | Ala | Gly | Ser | Ala | Ala | Lys | Ala | Asp | Met | Lys | Ala | Leu |
| | | | | 325 | | | | | 330 | | | | | 335 | |
| Leu | Lys | Ala | Ala | Ser | Glu | Gly | Ser | Asp | Gly | Ala | Ser | Leu | Thr | Phe | Asn |
| | | | 340 | | | | | 345 | | | | | 350 | | |
| Gly | Thr | Glu | Tyr | Thr | Ile | Ala | Lys | Ala | Thr | Pro | Ala | Thr | Thr | Pro |
| | | 355 | | | | | 360 | | | | | 365 | | |

Val Ala Pro Leu Ile Pro Gly Gly Ile Thr Tyr Gln Ala Thr Val Ser
370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
            405                 410                 415

Gly Glu Ser Ser Asp Ala Ala Lys Ser Tyr Val Asp Lys Gly Gly
                420                 425                 430

Ile Thr Asn Val Ala Asp Tyr Thr Val Ser Tyr Ser Val Asn Lys Asp
                435                 440                 445

Asn Gly Ser Val Thr Val Ala Gly Tyr Ala Ser Ala Thr Asp Thr Asn
450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
                485                 490                 495

Pro Leu Ala Ala Leu Asp Asp Ala Ile Ser Ser Ile Asp Lys Phe Arg
                500                 505                 510

Ser Ser Leu Gly Ala Ile Gln Asn Arg Leu Asp Ser Ala Val Thr Asn
                515                 520                 525

Leu Asn Asn Thr Thr Thr Asn Leu Ser Glu Ala Gln Ser Arg Ile Gln
530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
                580                 585

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccggatcctc tgcgctgtcg agttctatcg                                   30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccaagctttt aaccctgcag cagagac                                      27

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      6xHN tag -continued

```
<400> SEQUENCE: 5

His Asn His Asn His Asn His Asn His Asn His Asn
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```

IMMUNOGENIC COMPOSITIONS CONTAINING ESCHERICHIA COLI H7 FLAGELLA AND METHODS OF USE THEREOF

CROSS-REFERENCE TO RELATED APPLICATIONS

This application is a National Stage application of PCT/GB2008/003515, filed Oct. 17, 2008, which claims the priority of Great Britain Patent Application No. 0720250.0, filed Oct. 17, 2007. The foregoing applications are incorporated by reference herein in their entirety.

FIELD OF THE INVENTION

The present invention relates to the protein H7 from E. coli, especially O157, and related proteins, for use in immunising animals against E. coli, especially O157 and other EHEC strains. Desirably the use of H7 or related proteins reduces colonisation and/or shedding of bacteria from the gut. Conveniently administration is by way of parental administration and preferably H7 may be in the form of a fusion protein.

BACKGROUND OF THE INVENTION

Shiga toxin-producing strains of enterohaemorrhagic Escherichia coli (EHEC) are a class of pathogenic E. coli responsible for numerous food- and water-borne disease outbreaks although other transmission routes are also evident. EHEC causes a range of illnesses from non-bloody diarrhoea through haemorrhagic colitis to severe life-threatening haemolytic uremic syndrome (reviewed in (Nataro and Kaper, Diarrheagenic Escherichia coli, Clin Microbiol Rev 11: 142-201 (1998); Paton and Paton, Pathogenesis and diagnosis of Shiga toxin-producing Escherichia coli infections, Clin Microbiol Rev 11: 450-79 (1998)). Strains of EHEC O157:H7, the most common serotype causing human disease, remain an important cause of zoonotic infection throughout Northern Europe, North America and Japan in particular.

Attachment to the intestinal epithelium surfaces is an important initial step in pathogenesis of EHEC. The EHEC intimate adherence and A/E lesion formation in vitro and in vivo is mediated by the locus of enterocyte effacement (LEE) pathogenicity island, which encodes a type III protein secretion system. One of the LEE-encoded type III secreted proteins (Tir) is translocated into the host cell where it forms a hairpin structure in the host cell plasma membrane with an extracellular loop and two amino- and carboxy-terminal transmembrane domains (Kenny et al., Enteropathogenic E. coli (EPEC) transfers its receptor for intimate adherence into mammalian cells, Cell 91: 511-20 (1997); de Grado et al., Identification of the intimin-binding domain of Tir of enteropathogenic Escherichia coli, Cell Microbiol 1: 7-17 (1999)). The extracellular loop of Tir interacts directly with the LEE-encoded outer membrane protein intimin, thus anchoring the bacteria tightly to the host cell (de Grado et al., (1999)). The cytoplasmic domains of Tir binds to the host cytoskeletal and signalling proteins and initiate actin polymerization at the site of bacterial attachment (Goosney, et al., Recruitment of cytoskeletal and signaling proteins to enteropathogenic and enterohemorrhagic Escherichia coli pedestals, Infect Immun 69: 3315-22 (2001); Gruenheid et al., Enteropathogenic E. coli Tir binds Nck to initiate actin pedestal formation in host cells, Nat Cell Biol 3: 856-9 (2001) Campellone K G et al., EspF$_U$ is a translocated EHEC effector that interacts with Tir and N-WASP and promotes Nck-independent actin assembly, Dev Cell. 2004 August; 7(2):217-28). This results in the formation of actin pedestal structures underneath adherent bacteria.

Although a substantial amount of data has been generated in recent years regarding the interaction of E. coli O157:H7 with host cells, so far type III secretory proteins are the only O157:H7 virulence determinants demonstrated to play a direct role in attachment to intestinal mucosa in vivo. However, their role in intimate adherence is likely to be limited to later stages of infection (Donnenberg et al., The role of the eae gene of enterohemorrhagic Escherichia coli in intimate attachment in vitro and in a porcine model, J Clin Invest 92: 1418-24 (1993); McKee et al., The role of the eae gene of enterohemorrhagic Escherichia coli in intimate attachment in vitro and in a porcine model, J Clin Invest 92: 1418-24 (1995); Tzipori et al., The role of the eaeA gene in diarrhea and neurological complications in a gnotobiotic piglet model of enterohemorrhagic Escherichia coli infection, Infect Immun 63: 3621-7 (1995)) and factors conferring initial interaction of EHEC with intestinal epithelium remain to be clearly defined. Some people believe that EspA-containing surface appendages are important in initiating contact between EHEC and their target cells. After initial contact there is a gradual reduction in these filaments which are later replaced by tighter attachment mediated by intimin (Ebel et al., Initial binding of Shiga toxin-producing Escherichia coli to host cells and subsequent induction of actin rearrangements depend on filamentous EspA-containing surface appendages, Mol Microbiol 30: 147-61 (1998)). Although the factors responsible may not be fully defined, it is clear that the molecular interactions of E. coli O157:H7 with intestinal epithelium are complex and multiphasic and likely involve multiple types of ligand-receptor contacts during the course of colonization.

Recently, evidence has been presented to support a role for E. coli flagella in adherence to epithelium, not merely via motility/chemotaxis, but directly as an adhesin (Giron et al., The flagella of enteropathogenic Escherichia coli mediate adherence to epithelial cells, Mol. Microbiol. 44: 361-379 (2002)). Specifically, purified H6 and H2 flagella of EPEC bound human epithelial cells, as assessed non-quantitatively by immunofluorescence, and anti-H6 flagella antibodies inhibit adherence of EPEC strain E. coli O127:H6 (E2348/69). The H6 fliC mutant show a 60% reduction in adherence and introduction of fliC gene from the EPEC strain into a K-12 strain conferred adherence reminiscent of localized adherence. Hence flagella are implicated in pathogenicity of EPEC for which roles in initial adherence and microcolony formation is proposed.

A recent article demonstrates that flagella deficient Shiga-toxigenic E. coli O113:H21 is less virulent than Shiga-toxigenic E. coli having normal flagellin in a streptomycin-treated mouse model (Rogers et al., Reduced virulence of an fliC mutant of Shiga-toxigenic Escherichia coli O113:H21, Infect. Immun. 74: 1962-66 (2006)). However, neither Rogers et al. nor others have demonstrated that EHEC flagella are useful in a vaccine in bovine to reduce colonization of EHEC, or that flagella can be used in a vaccine to help protect bovine from EHEC colonization. Because there is a lack of an effective vaccine to prevent or reduce colonization of EHEC in bovine, there is a need for such a vaccine.

BRIEF SUMMARY OF THE INVENTION

The present invention is based in part on observations by the present inventors that H7 from E. coli O157 can be used as an immunogen against colonisation and/or shedding of bacteria from the gut of an animal, especially a ruminant or bovine animal. Moreover, it has been observed that the H7 can be administered parentally, for ease of administration, and yet still be capable of raising a suitable gut mucosal and/or IgA immune response, which may be effective against subsequent oral challenge of bacteria. Additionally H7 can be administered parentally in the form of a fusion protein where the fusion protein comprises a portion of another protein, which other protein by itself does not or poorly elicits a mucosal and/or IgA response. The fusion of H7 to said other protein can result in augmentation of a mucosal and/or IgA response to the other protein.

In a first aspect there is provided use of *E. coli* H7, such as *E. coli* O157 for reducing *E. coli* colonization and/or shedding in bovids by administering to an animal an immunogenic composition containing recombinant H7 or H7 purified from *E. coli*. In accordance with this aspect of the invention the use may desirably reduce EHEC O157:H7 colonization and/or shedding of/from an animal's large intestine or rectum.

In accordance with an embodiment of the present invention, the immunogenic composition may comprise recombinant H7 or H7 purified from EHEC O157:H7.

In a further aspect of the present invention there is provided a use of *E. coli* H7 for preventing *E. coli* from colonizing an animal's large intestine or rectum. The *E. coli* can be O157:H7 or any other *E. coli* containing flagella FliC amino acid sequence that has a high percentage of identity or homology to the amino acid sequence of FliC from O157:H7 strain EDL933. In order to prevent *E. coli* from colonizing an animal's large intestine or rectum, one can administer to the animal an immunogenic composition containing purified H7, recombinantly produced H7, polypeptides with the amino acid sequence of SEQ ID NO: 1, polynucleotides which encode H7, polynucleotides with the nucleic acid sequence of SEQ ID NO: 2, cells containing H7 encoding polynucleotides in an expression vector, and/or antibodies to H7. The purified H7 may be isolated and purified from *E. coli* that naturally produces the desired H7.

Recombinantly produced H7 can be produced in any bacteria, virus, fungi, plant, phage, tissue culture cells, milk, or any other known technique. Antibodies can be obtained from any animal that produces antibodies and can be found in liquids such as milk, egg, egg white, egg yolk, etc. In accordance with the invention that the route of administration the immunogenic composition to the animal can be any route of administration, including nasally, orally, rectally, vaginally, parentally, including intramuscularly, intravenously, intraarterially, intraperitoneally, intradermally, and subcutaneously. Preferably the immunogenic composition is administered parentally.

Conveniently the use of H7 may serve to reduce the amount of *E. coli* shed from the large intestine or rectum of an animal by administering an immunogenic composition to the animal; the reduction in the amount of *E. coli* shed being compared to the amount of *E. coli* shed from an animal which did not receive the immunogenic composition. The polynucleotides which encode H7 can be introduced into the animal to be treated by any known mechanism, such as electroporation, injection, viral encapsulated, liposome encapsulated, and bacterial encapsulated. It is a further object of the invention that the method of administering the immunogenic composition to the animal can be any route of administration, including nasally, orally, rectally, vaginally, intramuscularly, intravenously, intraarterially, intraperitoneally, intradermally, and subcutaneously.

The invention may also serve to generate a protective immune response in an animal against *E. coli* by administering an immunogenic composition of this invention to the animal.

Desirably use of H7 may result in the prevention or reduction of *E. coli* from attaching to the cells of an animal, preferably the cells of the large intestine or rectum. The present invention may therefore serve to reduce *E. coli*, such as O157 from passing to humans via the food chain. Thus, the invention can also been seen as a method of improving meat for human consumption by reducing an amount of *E. coli* being present in the gut/rectum of an animal, prior to slaughter.

The present invention also provides an immunogenic composition of H7 from *E. coli*. It is preferable that the *E. coli* be EHEC O157:H7 but the H7 can come from any *E. coli* with the gene, FliC type H7. The immunogenic composition can be purified H7 isolated from *E. coli* that produces H7 naturally, recombinantly produced H7, recombinantly produced H7, polypeptides with the amino acid sequence of SEQ ID NO: 1, polynucleotides which encode H7, polynucleotides with the nucleic acid sequence of SEQ ID NO: 2, cells containing H7 encoding polynucleotides in an expression vector, and/or antibodies that bind to H7. The immunogenic composition can contain pharmaceutically acceptable diluents and, optionally, one or more adjuvants. Preferably the immunogenic composition comprises H7 in the form of a fusion protein.

The present invention also provides a method of immunising an animal against *E. coli*, such as *E. coli* O157, comprising the step of administering H7 to an animal, so as to induce an immune response. Desirably the immune response includes a mucosal immune response, such as the production of IgA, typically in the gut and/or rectum mucosa. Preferably the H7 may be (or is intended to be) administered parentally. Preferably the H7 is in the form of a fusion protein.

DETAILED DESCRIPTION OF THE INVENTION

This invention involves uses and methods of using recombinantly produced H7, or H7 purified from *E. coli*, such as, O157:H7, or H7 produced in other bacteria or viruses or within the animal to induce an immune response to H7 within the animal. The immune response produced is sufficient to prevent *E. coli* O157:H7 from colonizing the animal, or to reduce the amount of *E. coli* O157:H7 colonizing the animal, or to reduce the shedding of *E. coli* O157:H7 from the animal which received the pharmaceutical composition or immunogenic composition containing H7 or containing DNA which encodes H7. The immune response may also be sufficient to reduce the symptoms of the disease caused by *E. coli* O157:H7, or to treat the animal which has been infected with *E. coli* O157:H7. The immune response may also be sufficient to reduce the amount of *E. coli* O157:H7 found within a herd or group of animals.

In addition, one can use passive immunity to protect nave animals against colonization of *E. coli* and/or reduce the amount of *E. coli* shed by the cattle. For passive immunity, one administers an immunogenic composition containing purified H7 or recombinant H7 to an animal, such as heifers, chickens, quails, etc., and collect the antibodies produced as expressed in the heifer's milk or in the bird's egg. Then one feeds the milk or egg which contains the antibodies to the nave animal, usually a new-born, to protect against or prevent colonization of *E. coli*.

The flagella of *E. coli* O157:H7 contains FliC type H7 as the major structural protein. H7 is encoded by the gene, fliC. The amino acid sequence for H7 from *E. coli* O157:H7 strain EDL933 is found in SEQ ID NO: 1 and the DNA sequence is found in SEQ ID NO: 2. H7 sequences from ten other O157: H7 strains are identical, hence epitopes are conserved between isolates. See Table 1 for the list of O157:H7 strains and the GenBank accession numbers for the sequences.

TABLE 1

| Strain | GenBank Accession | Serotype |
|---|---|---|
| EDL933 | AE005174 REGION: 2699591 . . . 2701348 | O157:H7 |
| Sakai (RIMD 0509952) | NC_002695 REGION: 2624379 . . . 2626136 | O157:H7 |
| TT12B | AM228905 | O157:H7 |
| NCTC12900 | AM228904 | O157:H7 |
| Walla Walla 3 | AM228903 | O157:H7 |
| 51 | AY337468 | O157:H7 |
| EH7 | AF228488 | O157:H7 |
| C664-1992 | AF228487 | O157:H7 |
| CL8 | AF128953 | O157:H7 |
| E32511 | U47614 | O157:H7 |
| DEC3a | AF128950 | O157:H7 |

Other serotypes of *E. coli* have flagella with extremely similar, if not identical, amino acid sequences to FliC from *E. coli* O157:H7 strain EDL933. As such, one can use the protein from those flagella as one would use FliC from *E. coli* O157: H7 strain EDL933, as described herein. Table 2 lists the strains, serotypes, and GenBank accession numbers of the *E. coli* having flagella amino acid sequence that is greater than 97% identical to the amino acid sequence of FliC of strain EDL933. Furthermore, an immunogenic composition containing H7 from O157:H7 strain EDL933 should reduce the colonization of any *E. coli* with an H7 amino acid sequence with high percentage of identity or homology to the amino acid sequence of H7 from O157:H7 strain EDL933, the reduction being compared to non-vaccinated animals. The methods described herein should prevent or reduce *E. coli* colonization of an animal's large intestine and reduce the shedding of *E. coli* in the feces of that animal.

TABLE 2

| Strain | GenBank Accession | Serotype |
|---|---|---|
| DEC 3f | AF128957 | O157:NM |
| TB156 | AF228489 | O55:H7 |
| DEC5d | AF128951 | O55:H7 |
| U5-41 (Orskov) | L07388 | O1:K1:H7 |
| U5-41 | AY249992 | O1:H7 |
| A1107 | AF228492 | O2:H7 |
| A64 | AF228494 | O7:H7 |
| D-M3291-54 | AF228493 | O18ac:H7 |
| A62 | AF228491 | O18ac:H7 |
| A57 | AF228490 | O18ac:H7 |
| F8188-41 | AF228495 | O19ab:H7 |
| 14097 | AF228496 | O53:H7 |
| DEC13a | AF128947 | O128:H7 |
| ECOR 37 | AF128958 | NT:H7 |
| UTI89 | NC_007946<br>REGION: 2025856 . . . 2027613 | NK:H7 |

NT—not typeable
NK—not known

One can use H7 obtained from *E. coli* O157:H7, or produced by another bacteria, virus, fungi, plant or other organism that contains an expression vector containing DNA that encodes H7. If the H7 is produced by an organism other than *E. coli* O157:H7, then one can use purified H7 or non-purified H7, depending on the protocol. It is understood that H7 may be contained within a fusion protein. Any reference to H7 includes a fusion protein containing H7. Various examples are set out below.

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "animal" refers to agriculturally/commercially important animals such as, for example, those belonging to the order Artiodactyla (the even-toed ungulates).

More specifically, the invention concerns members of the suborders "Suina" and "Ruminantia" which include species more commonly known as pigs and ruminants such as, for example, cattle, sheep, deer and goats.

Other agriculturally/commercially important animals to be considered as relevant to the present invention may include fowl or poultry such as chickens, turkeys, ducks, pheasants, game birds, geese and the like.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schinner., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include: (i) a positively-charged group containing Lys, Arg and H is, (ii) a negatively-charged group containing Glu and Asp, (iii) an aromatic group containing Phe, Tyr and Trp, (iv) a nitrogen ring group containing His and Trp, (v) a large aliphatic nonpolar group containing Val, Leu and De, (vi) a slightly-polar group containing Met and Cys, (vii) a small-residue group containing Ser, Thr, Asp, Asn, Gly, Ala, Glu, Gln and Pro, (viii) an aliphatic group containing Val, Leu, De, Met and Cys, and (ix) a small, hydroxyl group containing Ser and Thr.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The polynucleotide sequences encoding the fusion protein may be operably linked in frame so that the fusion protein may be translated correctly. A fusion protein may include polypeptide sequences from the same species or from different species. In various embodiments, the fusion polypeptide may contain one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides containing a glutathione S-transferase tag (GST-tag), histidine tag (His-tag), an immunoglobulin domain or an immunoglobulin binding domain.

Desirably the "fusion protein" or "fusion polypeptide" comprises H7, or immunogenic fragment thereof together with a further protein or protein fragment which does not or poorly elicits a mucosa/IgA immune response. Without wishing to be bound by theory, it is expected that fusing a further protein or protein fragment to H7 can increase/augment a mucosal/IgA immune response to said further protein/protein fragment, and/or reduce/eliminate a requirement for a separate adjuvant.

In addition, the present inventors have determined that the activation of Toll-like receptor-5 (TLR5) plays an important role in the generation of a mucosal and/or IgA response. As such, in one embodiment of this invention, the H7 protein or fragment (s) thereof and/or fusion proteins provided by this invention (i.e. the H7 protein fused to another protein or antigen) possess a TLR5 binding domain and exhibit an ability to activate TLR5. One of skill in this field will understand that the level of TLR5 activation exhibited by an H7 protein or H7 fusion protein as provided by this invention, may readily be determined by analysing the level of cytokines produced by certain cell lines. For example, the release of interleukin-8 (IL-8) by Caco-2 cells may be indicative of the level of TLR5 activation.

Fusion proteins provide by this invention may be generated by fusing a protein (for example an antigen) to the N-terminus or C-terminus of the H7 protein (or fragment thereof) or by inserting a protein (for example an antigen) into an internal region of the H7 protein. It should be understood that the term "internal" means any position within the H7 protein between the N-terminus and C-terminus. In other embodiments, it may be necessary to create an H7 fusion protein in which the other protein fused to the H7 protein is positioned or fused in such a way so as to not damage, disrupt or alter one or more of the functional/structural domains of the H7 protein. By way of example, and in order to generate H7 fusion proteins which retain or exhibit some TLR5 activity, it may be necessary to ensure that the other protein to be fused to the H7 protein, does not damage, disrupt or alter the TLR5 domain of the H7 protein.

In view of the above, H7 fusion proteins of this invention may comprise an H7 protein and another protein fused to the N-terminus or C-terminus. In this way, the TLR5 domain of the H7 protein is not damaged, disrupted or altered by the other protein. Preferably, the other protein is fused to the C-terminus of the H7 protein.

In a further embodiment, the H7 fusion proteins provided by this invention may comprise an H7 protein and another protein fused to or inserted into the variable region or domain of the H7 protein. In this way, the TLR5 domain of the H7 protein is not damaged, disrupted or altered by the other protein. Advantageously, restriction sites present within the H7 protein, but not present within the TLr5 domain of the H7 protein may be exploited as a means of fusing or inserting proteins to/into the 1-17 protein. In one embodiment, and in the case of H7 proteins which have the nucleic acid/amino acid sequences of SEQ ID NOS: 1/2, the Acc-1 restriction sites present in the variable region (and not in the TLR5 domain) may be used to generate a fusion protein according to this invention.

Suitable further or other proteins/protein fragments may be other surface expressed proteins from *E. coli*, such as intimin, EspA, B and D, efa-1, Iha, outer membrane proteins, O-antigens and porins.

Other proteins may include proteins, such as surface proteins, from other organisms which may invade a host by way of its gut or other mucosal surface including other bacteria, nematodes and viruses. Specific viral proteins include the major envelope glycoprotein (E2) of Bovine Viral diarrhoea Virus, the F protein of Bovine Respiratory Syncitial Virus (BRSV), the gB and gD glycoproteins of Bovine Herpes Virus-1 (BHV-1), and the F and HN proteins of bovine parainflueza-3 (PI-3) virus. Other enteric viruses include the S protein of Bovine Coronavirus and the VP4 protein of Bovine Rotavirus.

The term "isolated polypeptide" refers to a polypeptide, in certain embodiments prepared from recombinant DNA or RNA, or of synthetic origin or natural origin, or some combination thereof, which (1) is not associated with proteins that it is normally found with in nature, (2) is separated from the cell in which it normally occurs, (3) is free of other proteins from the same cellular source, (4) is expressed by a cell from a different species, or (5) does not occur in nature. It is possible for an isolated polypeptide to exist but not qualify as a purified polypeptide.

The term "isolated nucleic acid" and "isolated polynucleotide" refers to a polynucleotide whether genomic DNA, cDNA, mRNA, tRNA, rRNA, iRNA, or a polynucleotide obtained from a cellular organelle (such as mitochondria and chloroplast), or whether from synthetic origin, which (1) is not associated with the cell in which the "isolated nucleic acid" is found in nature, or (2) is operably linked to a polynucleotide to which it is not linked in nature. It is possible for an isolated polynucleotide to exist but not qualify as a purified polynucleotide.

The term "nucleic acid" and "polynucleotide" refers to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" and "polynucleotide of the invention" refers to a nucleic acid encoding H7 or a mutant, fragment, variant, or derivative thereof. A polynucleotide of the invention may comprise all, or a portion of, a subject nucleic acid sequence; a nucleotide sequence at least 60%, 70%, 80%, 90%, 95%, 96%, 97%, 98% or 99% (and every single digit between 60 and 100) identical to a subject nucleic acid sequence; a nucleotide sequence that hybridizes under stringent conditions to a subject nucleic acid sequence; nucleotide sequences encoding polypeptides that are functionally equivalent to polypeptides of the invention; nucleotide sequences encoding polypeptides at least about 60%, 70%, 80%, 85%, 90%, 95%, 98%, 99% (and every single digit between 60 and 100) homologous or identical with a subject amino acid sequence; nucleotide sequences encoding polypeptides having an activity of a polypeptide of the invention and having at least about 60%, 70%, 80%, 85%, 90%, 95%, 98%, 99% or more (and every single digit between 60 and 100) homology or identity with a subject amino acid sequence; nucleotide sequences that differ by 1 to about 2, 3, 5, 7, 10, 15, 20, 30, 50, 75 or more nucleotide substitutions, additions or deletions, such as allelic variants, of a subject nucleic acid sequence; nucleic acids derived from and evolutionarily related to a subject nucleic acid sequence; and complements of, and nucleotide sequences resulting from the degeneracy of the genetic code, for all of the foregoing and other nucleic acids of the invention. Nucleic acids of the invention also include homologs, e.g., orthologs and paralogs, of a subject nucleic acid sequence and also variants of a subject nucleic acid sequence which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a domain having the desired biological activity, and optionally additional amino acids on one or both sides of the domain, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide containing the amino acid sequence of H7, or an equivalent or fragment thereof. Polypeptides of the invention include polypeptides containing all or a portion of H7 amino acid sequence; an amino acid sequence with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% (and every single digit between 60 and 100) homologous or identical to H7 amino acid sequence; and functional fragments thereof. Polypeptides of the invention also include homologs, e.g., orthologs and paralogs, of a subject amino acid sequence. Polypeptides of the invention include fusion proteins containing H7.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

The term "purified" refers to an object species that is the predominant species present (i.e., on a molar basis it is more abundant than any other individual species in the composition). A "purified fraction" is a composition wherein the object species is at least about 50 percent (on a molar basis) of all species present. In making the determination of the purity or a species in solution or dispersion, the solvent or matrix in which the species is dissolved or dispersed is usually not included in such determination; instead, only the species (including the one of interest) dissolved or dispersed are taken into account. Generally, a purified composition will have one species that is more than about 80% of all species present in the composition, more than about 85%, 90%, 95%, 99% or more of all species present. The object species may be purified to essential homogeneity (contaminant species cannot be detected in the composition by conventional detection methods) wherein the composition is essentially a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase (e.g., Pho5), the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids or nucleotides occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups).

The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams of more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology or identity between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C.

However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((3 \times \#GC)+(2 \times \#AT)) \times 37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution containing 50% formamide, 10×Denhardts (0.2% Ficoll, 0.2% polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in Biochemistry and Molecular Biology—Hybridization With Nucleic Acid Probes, e.g., part I chapter 2 "Overview of principles of hybridization and the strategy of nucleic acid probe assays", Elsevier, New York; and Tibanyenda, N. et al., Eur. J. Biochem. 139:19 (1984) and Ebel, S. et al., Biochem. 31:12083 (1992).

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In another aspect of the invention, the polynucleotide of the invention is provided in an expression vector containing a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

An expression vector containing the polynucleotide of the invention can then be used as a pharmaceutical agent or immunogenic agent to treat an animal infected with E. coli O157:H7 or as a vaccine (also a pharmaceutical agent or immunogenic agent) to prevent an animal from being infected with E. coli O157:H7, or to reduce the symptoms and course of the disease if the animal does become infected or to reduce the shedding of E. coli O157:H7 from the animal or reduce the colonization of E. coli O157:H7 in the animal. One manner of using an expression vector as a pharmaceutical or immunogenic agent is to administer a nucleic acid vaccine to the animal at risk of being infected or to the animal after being infected. Nucleic acid vaccine technology is well-described in the art. Some descriptions can be found in U.S. Pat. No. 6,562,376 (Hooper et al.); U.S. Pat. No. 5,589,466 (Feigner, et al.); U.S. Pat. No. 6,673,776 (Feigner, et al.); and U.S. Pat. No. 6,710,035 (Feigner, et al.). Nucleic acid vaccines can be injected into muscle or intradermally, can be electroporated into the animal (see WO 01/23537, King et al.; and WO 01/68889, Malone et al.), via lipid compositions (see U.S. Pat. No. 5,703,055, Feigner, et al.), or other mechanisms known in the art field.

Expression vectors can also be transfected into bacteria, which can be administered to the target animal to induce an immune response to the protein encoded by the nucleotides of this invention contained on the expression vector. The expression vector can contain eukaryotic expression sequences such that the nucleotides of this invention are transcribed and translated in the host animal. Alternatively, the expression vector can be transcribed in the bacteria and then translated in the host animal. The bacteria used as a carrier of the expression vector should be attenuated but still invasive. One can use Shigella spp., Salmonella spp., Escherichia spp., and Aeromonas spp., just to name a few, that have been attenuated but still invasive. Examples of these methods can be found in U.S. Pat. No. 5,824,538 (Branstrom et al.); U.S. Pat. No. 5,877,159 (Powell, et al.); U.S. Pat. No. 6,150,170 (Powell, et al.); U.S. Pat. No. 6,500,419 (Hone, et al.); and U.S. Pat. No. 6,682,729 (Powell, et al.). Such live, attenuated bacteria may be preferable for inducing a mucosal immune response to H7 contained on the eukaryotic expression vector.

Alternatively, an expression vector containing DNA that encodes H7 can be expressed in prokaryotes by culturing the bacteria such that the expression vector is activated and H7 is produced. Then one can administer the bacteria, which contain H7 to the animal to induce an immune response to H7. H7 can be expressed as an outer membrane protein or cytosolic protein, or found within inclusion bodies. The animal may generate an immune response in the mucosal tissue or systemically after administration of prokaryotes expressing H7.

Alternatively, the polynucleotides of this invention can be placed in certain viruses, which act a vector. Viral vectors can either express the proteins of this invention on the surface of the virus, or carry polynucleotides of this invention into an animal cell where the polynucleotide is transcribed and translated into a protein. The animal infected with the viral vectors can develop an immune response to the proteins encoded by the polynucleotides of this invention. Thereby one can alleviate or prevent an infection by *E. coli* O157:H7 in the animal which received the viral vectors. Examples of viral vectors can be found U.S. Pat. No. 5,283,191 (Morgan et al.); U.S. Pat. No. 5,554,525 (Sondermeijer et al.) and U.S. Pat. No. 5,712,118 (Murphy).

The polynucleotide of the invention may be used to cause expression and over-expression of a polypeptide of the invention in cells propagated in culture, e.g. to produce proteins or polypeptides, including fusion proteins or polypeptides.

This invention pertains to a cell transfected with a recombinant gene in order to express a polypeptide of the invention. The cell may be any prokaryotic or eukaryotic cell. For example, a polypeptide of the invention may be expressed in bacterial cells, such as *E. coli*, insect cells (baculovirus), yeast, plant, or mammalian cells. In those instances when the cell is human, it may or may not be in a live subject. Other suitable cells are known to those skilled in the art. Additionally, the cell may be supplemented with tRNA molecules not typically found in the cell so as to optimize expression of the polypeptide. Alternatively, the nucleotide sequence may be altered to optimize expression in the cell, yet the protein produced would have high homology to the originally encoded protein. Other methods suitable for maximizing expression of the polypeptide, will be known to those in the art.

The present invention further pertains to methods of producing the polypeptides of the invention. For example, a cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into cells or organisms, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Suitable vectors for the expression of a polypeptide of the invention include plasmids of the types: pTrcHis-derived plasmids, pET-derived plasmids, pBR322-derived plasmids, pEMBL-derived plasmids, pEX-derived plasmids, pBTac-derived plasmids and pUC-derived plasmids for expression in prokaryotic cells, such as *E. coli*. The various methods employed in the preparation of the plasmids and transformation of organisms are well known in the art. For other suitable expression systems for both prokaryotic and eukaryotic cells, as well as general recombinant procedures, see *Molecular Cloning, A Laboratory Manual,* 2nd Ed., ed. by Sambrook, Fritsch and Maniatis (Cold Spring Harbor Laboratory Press, 1989) Chapters 16 and 17.

Coding sequences for a polypeptide of interest may be incorporated as a part of a fusion gene including a nucleotide sequence encoding a different polypeptide. The present invention contemplates an isolated polynucleotide containing a nucleic acid of the invention and at least one heterologous sequence encoding a heterologous peptide linked in frame to the nucleotide sequence of the nucleic acid of the invention so as to encode a fusion protein containing the heterologous polypeptide. The heterologous polypeptide may be fused to (a) the C-terminus of the polypeptide of the invention, (b) the N-terminus of the polypeptide of the invention, or (c) the C-terminus and the N-terminus of the polypeptide of the invention. In certain instances, the heterologous sequence encodes a polypeptide permitting the detection, isolation, solubilization and/or stabilization of the polypeptide to which it is fused. In still other embodiments, the heterologous sequence encodes a polypeptide such as a poly His tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

Preferred polypeptides of the invention will have one or more biological properties (e.g., in vivo, in vitro or immunological properties) of the native full-length polypeptide. Non-functional polypeptides are also included within the scope of the invention because they may be useful, for example, as antagonists of the functional polypeptides. The biological properties of analogues, fragments, or derivatives relative to wild type may be determined, for example, by means of biological assays. Polypeptides, including analogues, fragments and derivatives, can be prepared synthetically (e.g., using the well known techniques of solid phase or solution phase peptide synthesis). Preferably, solid phase synthetic techniques are employed. Alternatively, the polypeptides of the invention can be prepared using well known genetic engineering techniques, as described infra. In yet another embodiment, the polypeptides can be purified (e.g., by immunoaffinity purification) from a biological fluid, such as but not limited to plasma, faeces, serum, milk, egg components, or urine from animals, including, but not limited to, pig, chicken, goose, duck, quail, turkey, parakeet, human, monkey, dog, cat, horse, hamster, gerbil, rabbit, ferret, horse, cattle, and sheep. An animal can be any mammal or bird.

The polypeptide analogues include those polypeptides having the amino acid sequence, wherein one or more of the amino acids are substituted with another amino acid which substitutions do not substantially alter the biological activity of the molecule.

According to the invention, the polypeptides of the invention produced recombinantly or by chemical synthesis and fragments or other derivatives or analogues thereof, including fusion proteins, may be used as an immunogen to generate antibodies that recognize the polypeptides.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be the portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for the antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "protective immune response" refers to an immune response in an animal that protects the animal from an infection with the infectious agent against which the animal was immunized. It also refers to an immune response in the animal that reduces or ameliorates the symptoms of disease that is caused by the infection of the infectious agent against which the animal is immunized, where the reduction is compared to non-immunized or naïve animal that become infected. For example, suppose a bacteria or virus cause a disease in an animal which is characterized by the animal reduces food intake, becomes lethargic, loses weight, has a fever, has diarrhea, shedding of the infectious agent, or has nasal discharge. Then an animal which receives the immunogenic composition of this invention and has protective immunity or a protective immune response would have greater food intake, be more active, loses less weight or gains weight, has a reduced fever or no fever, has less diarrhea or no diarrhea, has reduced or no shedding of the infectious agent, or has less nasal discharge or no nasal discharge when exposed or infected with the pathogen as compared to an animal that was not immunized and is exposed or infected with the pathogen.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvunz*. Preferably, the adjuvant is pharmaceutically acceptable.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical or immunogenic compositions comprising therapeutically effective amounts of the amino acid sequences described herein or an analogue, fragment or derivative product thereof or fusion protein, or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hyluronic acid may also be used. Such compositions may influence the physical state, stability, rate of in vivo release, and rate of in vivo clearance of the present proteins and derivatives. See, e.g., *Martin, Remington's Pharmaceutical Sciences,* 18th Ed. (1990, Mack Publishing Co., Easton, Pa. 18042) pages 1435-1712 that are herein incorporated by reference. The compositions may be prepared in liquid form, or may be in dried powder, such as lyophilised form. H7 protein or an expression vector encoding H7 may be coated onto beads or within polymers which are administered to the animal in various routes.

The polynucleotides of the invention can also be optimized for expression in plants (e.g., corn). The plant may be transformed with plasmids containing the optimized polynucleotides. Then the plant is grown, and the proteins of the invention are expressed in the plant, or the plant-optimized version is expressed. The plant is later harvested, and the section of the plant containing the proteins of the invention is processed into feed for the animal. This animal feed will impart immunity against *E. coli* O157:H7 when eaten by the animal. Examples of prior art detailing these methods can be found in U.S. Pat. No. 5,914,123 (Arntzen, et al.); U.S. Pat. No. 6,034,298 (Lam, et al.); and U.S. Pat. No. 6,136,320 (Arntzen, et al.).

It will be appreciated that pharmaceutical or immunogenic compositions provided according to the invention may be administered by any means known in the art. Preferably, the pharmaceutical or immunogenic compositions for administration are administered by injection, orally, rectally, vaginally, or by the pulmonary, or nasal route. The amino acid sequences described herein or expression vectors are more preferably delivered by a parental route, e.g. intravenous, subcutaneous, intraarterial, intraperitoneal or intramuscular. Parental administration is preferred due to the desirability of such an administration to agriculture animals, such as cows, sheep, goats and pigs. Unexpectedly, such administration can lead to a significant mucosal/IgA immune response, which can be effective when animals are subsequently orally challenged by further bacteria. Any known route that stimulates a mucosal immune response or enough of a system immune response such that there is an affect in the mucosal tissue is preferable.

For rectal administration, the H7 antigen can be coated or incorporated into beads which are inserted into the rectum of the animal. The beads can be contain of either poly(D,L-lactide-co-glycolide)(PLG) polymer, chitosan, alginate, liposomes or similar, which have been extensively employed to generate micro or nanobeads for the purposes of stimulating mucosal immune responses. The beads (microbeads <20 μm in mean diameter but > than 1 μm, or nanobeads <1 μm in mean diameter), may be administered on several (up to 6) occasions, with each dose providing between 10-1000 micrograms of protein. The volume of each intra-rectal administration will be between 0.1 ml and 10 ml. Beads may also contain additional defined proteins, to act as mucosal adjuvants, such as cholera toxin.

The full length FliC (H7), immunogenic fragments thereof and/or fusion proteins containing either the full length or immunogenic fragments of FliC are intended for use in the immunogenic compositions of this invention. The proteins and peptides of the invention may be prepared using recombinant DNA methods. Nucleic acid molecules of the present invention having a sequence which encodes FliC(H7) or fragments thereof may be incorporated into an expression vector or other replicon to ensure expression of the protein/peptide. The expression vector containing the fragments can be expressed in biological systems including bacteria, yeast, viruses, eukaryotic cell cultures, plants, insects or in vitro. Several of the expression vectors used contain control sequences that allow for regulated expression of the protein/peptide in response to a chemical or physical stimulus. Fusion proteins are used to simplify the purification process either in the initial fractionation or by providing an affinity tag that can be used to isolate and concentrate the protein/peptide, or by aiding in the secretion of the fusion protein from the cell into the media. The term expression vector means a replicon, such as a plasmid, phage, cosmid or BAC clone, into which another DNA segment can be integrated to bring about the replication of the integrated segment. The expression vector plus integrated FliC(H7) protein/peptide sequence will contain a nucleic acid sequence (promoter) that promotes transcription through the target sequence reading frame. The mRNA produced will have relevant sequences to initiate translation of the target protein/peptide.

Non-limiting examples of recombinant DNA expression vectors used for cloning and protein/peptide expression in bacteria include expression vectors that initiate expression using lac, tac, T7, T5, or SP6 promoters. For fusion proteins, the following are non-limiting examples of the peptide/protein tags that can be added to the target peptide/protein: 6XHN (SEQ ID NO: 5), histidine tags, biotin tags, calmodulin binding protein, cellulose binding protein, maltose binding protein, dihydrofolate-reductase, intein-chitin binding domain, T7 gene 10, hemagglutinin tag, FLAG tags, glutathione S-reductase. Examples of expression vectors include, but are not limited to, pACYC177 and all derivatives, pBR322 and all derivatives, pUC 18 and all derivatives, these may include: the pET series of vectors (Novagen); pFLAG and pTAC series (Sigma-Aldrich); pMAL and pTXB series (New England Biolabs); pGEMEX, pALTER and PIN-POINT series (Promega); pQE and QIAexpress series (Qiagen); pCAL series (Stratagene); pET, Gateway, and pBAD series (Invitrogen).

Depending on the expression system and the host selected, the protein/peptide of interest may be produced by growing cells, transformed or transfected by an expression vector as described above, under conditions that express the protein/peptide of interest. The protein/peptide may then be isolated from the host cells and purified. If the expression system secretes the protein into the growth medium, the protein is purified directly from this. If the protein is not secreted, then it is isolated from cell lysates. Protein expression can be carried out in a variety of bacterial species, but more commonly *Escherichia coli* strains are used, such as BL21 and derivatives that have reduced protease activity. *Bacillus* spp. and *Streptomyces* spp. are also used. *Saccharomyces* spp. and other yeasts are also used. Expression can be induced in mammalian cells for example by direct transfection or by infection with a recombinant virus containing the target sequences such as Baculo and papilloma viruses. The protein/peptide of interest may also be expressed in plants for purification or for direct consumption as an immunogenic composition. The plant maybe selected from various plant families including Brassicaceae, Compositae, Euphorbiaceae, Leguminosae, Linaceae, Malvaceae, Umbilliferae, Graminae, Nicotiana and Trifolium spp.

The proteins/peptides of interest may also be produced by chemical synthesis such as solid phase peptide synthesis.

Additionally, the H7 can be administered to an animal to generate antibodies to H7. The antibodies can be collected and then administered to another animal to provide that second animal with passive immunity. The antibodies may be found in eggs or milk in vaccinated animals that lay eggs or produce milk. The animal may need to be hyperimmunized with H7 in order to produce sufficient numbers of antibodies to H7.

The EHEC strains used in the examples below are as follows: ZAP 734 (Stx-negative E. coli O157:H7 strain NCTC 12900; also designated ZAP193), ZAP 735 (fliC-isogenic mutant derived from strain NCTC 12900) were gifted by Prof. Martin Woodward (Veterinary Laboratories Agencies, Weybridge UK). The fliC mutant was generated and its capacity to colonise during experimental infections has been assessed (Best A, et al.; Role for flagella but not intimin in the persistent infection of the gastrointestinal tissues of specific-pathogen-free chicks by Shiga toxin-negative Escherichia coli O157:H7; Infection and Immunity 73 (3):1836-1846 (March 2005); La Ragione R M, et al.; Colonization of 8-week-old conventionally reared goats by Escherichia coli O157:H7 after oral inoculation; J of Medical Microbiology 54 (5): 485-492 (May 2005); Best A, et al.; A comparison of Shiga-toxin negative Escherichia coli O157 aflagellate and intimin deficient mutants in porcine in vitro and in vivo models of infection; Veterinary Microbiology 113 (1-2): 63-72 (Mar. 10, 2006)), ZAP 196 (Stx-positive E. coli O157:H7 (Walla Walla 1) and ZAP 198 (Stx-negative E. coli O157:H7; Walla Walla 3) were supplied by Dr Mary Reynolds, Atlanta, USA, ZAP 244 (O113:H21) by Dr Elizabeth Hartland, Melbourne, Australia, ZAP 116 (O26:H11) by Prof. Tom Besser, Pullman, USA and EPEC strain ZAP 286 (E2348/69, O127: H6) by Dr Mark Stevens, Institute for Animal Health, Compton, UK.

The present invention will now be further described by way of example and with referent to the figures, which show:

FIG. 1 shows levels of H7 specific IgG and IgA measured by ELISA in serum, nasal secretions and rectal swab samples from calves following systemic immunisation with H7 flagellin. (A) serum IgG level; (B) serum IgA level; (C) nasal IgG level; (D) nasal IgA level; (E) rectal IgG level; and (F) rectal IgA level. The values represent the mean value±the standard error of the mean for eight calves at each time point. The solid arrows indicate the timing of immunizations; the open arrow indicates the timing of subsequent oral bacterial challenge with E. coli O157:H7. IM H7, i.m. H7; PR H7, rectal immunization with H7 in PBS; PR PLG:H7, rectal immunization with H7 encapsulated in PLG microparticles; NVC, non-vaccinated controls.

Legend:
—●— IM H7 —▲— PR H7 —○— PR PLG:H7 —△— NVC

Figure 4:
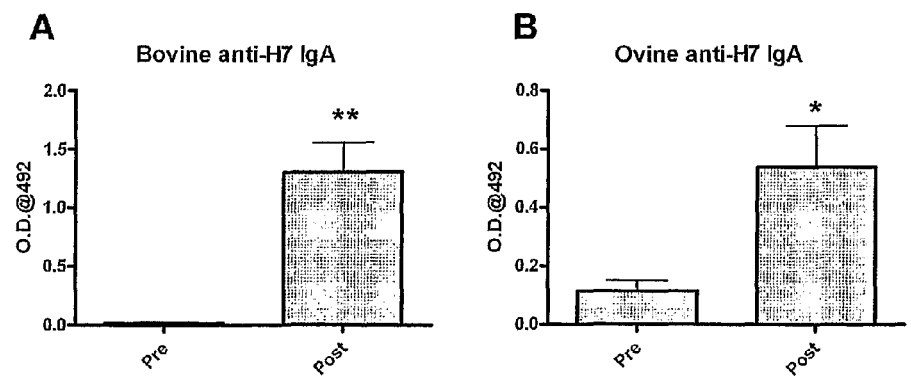

FIG. 4 shows Nasal IgA responses following intra-muscular immunization of calves (A) or sheep (B) with native H7 flagellin+5 mg Quil A adjuvant. Animals were immunized on 2 separate occasions 2 weeks apart. Nasal secretion samples were taken 2 days prior to immunization and 1 week after the second immunization and anti-H7 antibodies quantified by ELISA. (A) Significant increase in nasal anti-H7 IgA following immunization of calves with native H7 flagellin (n=8); (B) Significant increase in nasal anti-H7 IgA following immunization of sheep with native H7 flagellin (n=5). Data represents the mean value±SEM. * P<0.05; **; P<0.01 compared to pre-immunization levels, paired Student's t-test.

FIG. 5 (A) Nucleotide sequence of H7 flagellin (SEQ ID NO: 1). AccI restrictions sites underlined and in bold; (B) Amino acid sequence of H7 flagellin (SEQ ID NO: 2). Boxes shown TLR5 binding domains. Arrows indicate AccI restriction sites for insertion of antigen into the central variable region of H7 flagellin. Variable region is highlighted in grey.

Figure 6:
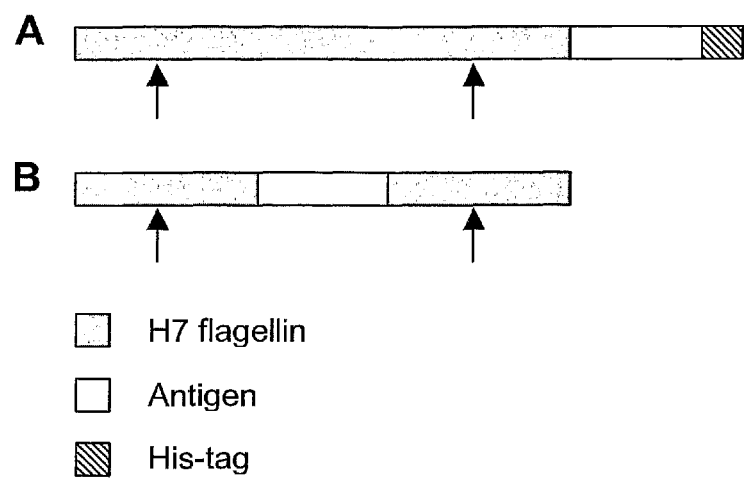

FIG. 6 Diagram demonstrating two strategies for the generation of H7 flagellin fusion proteins which retain TLR5 signaling activity. (A) Fusion of antigen to the C-terminus of H7 flagellin and inclusion of a terminal His-tag for subsequent protein purification. (B) Replacement of the central variable region of H7 flagellin with the fusion antigen. Protein is expressed following activation of the wild-type H7 promoter and exported into the culture supernatant. Arrows indicate the location of the TLR5 binding domains within the conserved N and C terminal regions of H7 flagellin.

Figure 7:
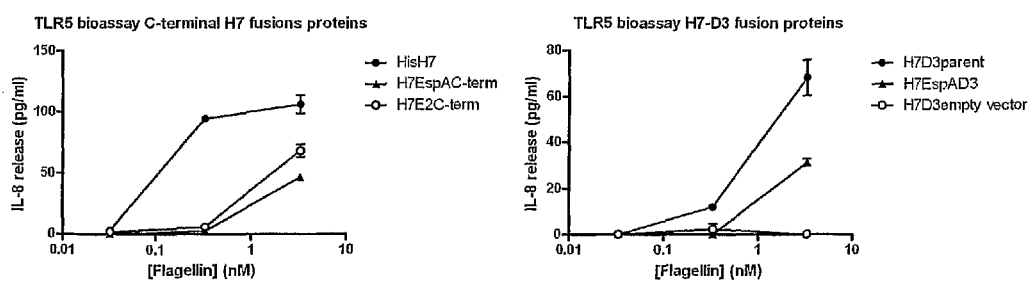

FIG. 7 Results from a TLR5 bioassay based on release of interleukin 8 (IL-8) into the supernatants of Caco-2 cell cultures following ligation of TLR5. Data represents the mean±standard error of the mean (n=6). (A) Challenge with his-tagged recombinant H7 alone (HisH7) or containing a C-terminal fusion of either EspA (H7EspAC-term) or E2 (H7E2C-term) results in release of IL-8 into the cell culture supernatant, indicative of TLR5 activation. (B) Challenge with recombinant H7 expressed via wild-type H7 promoter containing either no fusion (H7D3 parent) or an internal fusion of EspA (H7EspAD3) also results in release of IL-8 into the culture supernatant. IL-8 release was not observed following challenge of Caco-2 cells with an equivalent concentration of protein purified following transfection of bacteria with empty plasmid vector (H7D3 empty vector).

Figure 8:
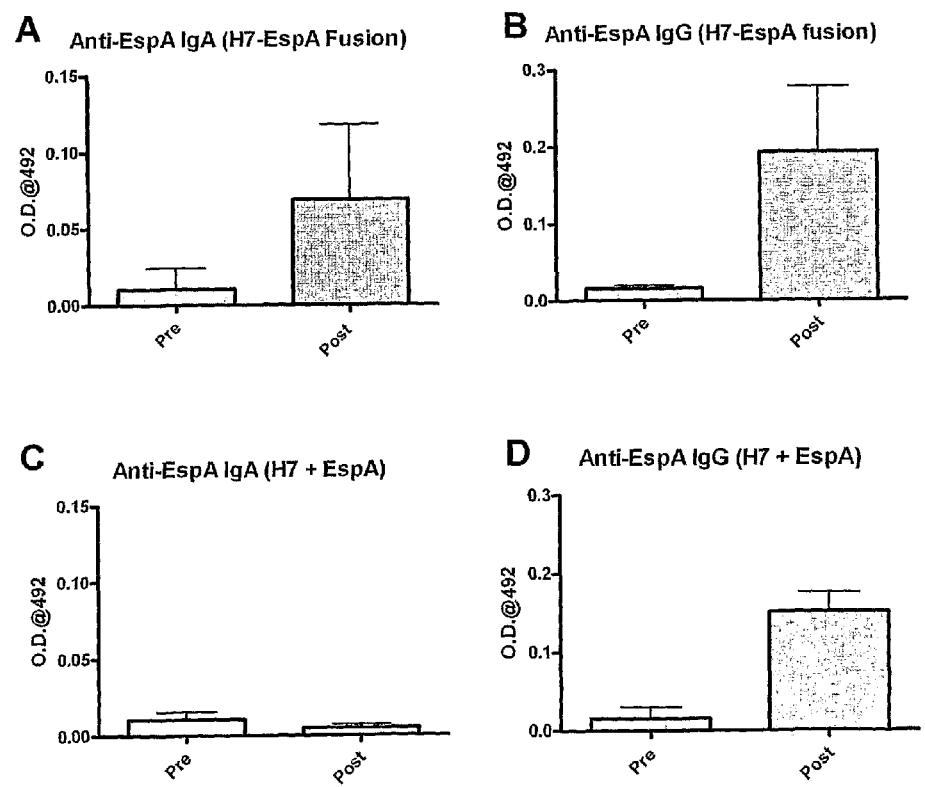

FIG. 8 Nasal antibody responses following intra-muscular immunization (IM) of calves with EspA fused to the C-terminus of H7 flagellin (H7-EspA Fusion) or EspA co-administered with H7 flagellin (H7+EspA), both in combination with 5 mg Quil A adjuvant. IM immunization with H7-EspA fusion protein results in both EspA-specific IgA and IgG antibody responses (A and B respectively). Co-immunization of EspA with unfused H7 induces an anti-EspA IgG response but no EspA-specific IgA response (C-D). Data represents the mean±SEM, n=3.

FIG. 9 Nasal IgA antibody responses following IM immunization of sheep with either native H7 flagellin (nH7), recombinant his-tagged H7 flagellin (reCH7), nematode antigen Tc-SAA fused to the C-terminus of H7 (H7-Tc-SAA) or Tc-SAA alone. Anti-H7 IgA responses were induced following immunization with nH7 and reCH7 but not H7-Tc-SAA or Tc-SAA (A). No nasal IgA responses to Tc-SAA were induced in any immunization group (B). The ability of the H7 antigens to activate TLR5 was subsequently assessed using an in vitro bioassay (C). Both native and recombinant H7 flagellin but not H7-Tc-SAA resulted in TLR5-dependent IL-8 release from Caco-2 cells. Data represents the mean±SEM. n=5 per group for immunizations and n=9 for TLR5 bioassay experiment. *, P<0.05 (paired Student's t-test).

FIG. 10: Dose response experiment showing potency of H7 to activate TLR5. This luciferase reporter assay detects TLR5 activity down 0.1 ng/ml H7

Example 1

E. coli O157 Lacking Flagella Exhibit Diminished Adherence to Bovine Rectal Primary Epithelial Cells To examine the role of H7 as an adhesin, the adherence of wild-type Stx-negative EHEC O157:H7 flagellate strain ZAP 734 (NCTC 12900), and of E. coli fliC-isogenic mutant strain ZAP 735 (derived from ZAP 734) to bovine rectal primary epithelial cells are compared.

Bovine rectal primary epithelial cells are cultured in D-valine containing special culture medium MEM w/o L-valine (Cell Culture Technologies Gmbh, Zurich Switzerland) supplemented with 2.5% fetal calf serum (Sigma-Aldrich Company Ltd., Gillingham, UK), 0.25 U/ml insulin (Sigma-Aldrich Company Ltd.), 10 ng/ml epidermal growth factor (EGF) (Sigma-Aldrich Company Ltd.) and 30 µg/ml gentamicin (Sigma-Aldrich Company Ltd.). The cells are grown on collagen-coated 24-well culture plates or 4-well chamber slides (Corning, Corning, N.Y.) until confluence with approximately $3 \times 10^5$ cells/well. It takes approximately 10 to 14 days following primary epithelial cell culture to obtain a state of confluence.

Overnight cultures of the bacterial strains ZAP 734 and ZAP 735 grown in Minimal Essential Medium Eagle with Earle's Salts (M7278, Sigma-Aldrich Company Ltd.) with 25 mM HEPES are diluted 1:10 and further grown to an optical density of 0.3-0.4 at $OD_{600}$ in a shaking incubator at 200 rpm at 37° C. for approximately 3 hours. The confluent bovine rectal primary epithelial cells are washed twice in pre-warmed MEM-HEPES. The bovine rectal primary epithelial cells are infected at a multiplicity of infection (MOI) of 1:100 in MEM-HEPES at 37° C., 5% $CO_2$ for 1 hour or 3 hours. The infected cells are washed three times with PBS to remove the non-adherent bacteria. Adherent bacteria are solubilised/removed by washing with PBS-0.1% (v/v) Triton X-100 at room temperature, serially diluted, and plated onto LB agar to determine the number of bacteria adhering to the cells in culture as colony forming units (cfu).

After 3 hours, the aflagellate ZAP 735 strain adhere sparsely and express no flagella compared to wild type ZAP 734 which demonstrate localized adherence with abundant expression of flagella and substantial microcolony formation. Adherent bacterial counts for wild type ZAP 734 are $3.95 \times 10^6$ cfu·ml$^{-1}$ compared to $1.27 \times 10^6$ for the fliC mutant ZAP 735 after 1 hour post infection (p=0.0001). At 3 hour post infection, adherent ZAP 734 counts are $3.47 \times 10^7$ compared to $6.59 \times 10^6$ for ZAP 735 (p=0.0001). To overcome any anomalies of initial cell-bacterium interaction, i.e., to determine whether this reduction in initial adherence of fliC-mutant was due to loss of motility, binding assays are carried out in which bacterial cells are centrifuged onto bovine rectal primary epithelial cells and, after a short incubation of 15 minutes, adherent bacteria were enumerated. Centrifugation of 1000 rpm for 3 minutes (centrifuge model GS-6R, Beckman, High Wycombe, Buckinghamshire, UK) is applied to infected cells in 24-well tissue culture plates. The mild centrifugation significantly enhances binding of both the flagellate wild type ZAP 734 and isogenic fliC mutant ZAP 735 strains (p<0.0001). Importantly, following centrifugation the wild type flagellate ZAP 734 strain still adhere significantly more than the aflagellate mutant (p<0.0003). Without centrifugation, adherent cfu for ZAP734 are $5.52 \times 10^5$ and for ZAP735 are $3.16 \times 10^5$. After centrifugation values were $1.2 \times 10^6$ and $8.69 \times 10^5$ respectively.

Example 2

E. coli O157 Lacking Flagella Exhibit Diminished Adherence to Tissue Explants from Terminal Rectal Mucosa To examine the role of flagella in binding of E. coli O157:H7 to bovine gut, an in vitro organ culture technique is used. Tissue specimens are obtained from adult cattle at a local abattoir and are transported in ice cold Hanks balanced saline solution (HBSS) (Gibco BRL, Gaithersburg, Md.). The terminal rectal mucosa 3 cm proximal to the recto-anal junction is carefully excised and washed in cold PBS, cut into 1 cm squares with a thickness of 2 mm and placed in tissue culture medium RPMI 1640 (RS886, Sigma-Aldrich Company Ltd.). The mucosal pieces are placed on a sterile foam pad and are immersed in pre-warmed (37° C.) RPMI 1640. The bacterial cultures are grown as described above for the adherence assays. The explants are infected with cultures of ZAP 734 or ZAP 735 strains (100 µl) for 8 hours at 37° C., 5% $CO_2$, 95% air in a humidified atmosphere. After 2 hours of infection the medium is replaced at every 1 hour interval. The infected tissue explants are washed 3× in PBS, and are fixed and permeabilized overnight (4° C.) in 4% (w/v) formalin/0.2% (v/v) Triton X-100 and stained by immunofluorescence. The bacteria adherent to the tissue are detected with primary rabbit anti-O157 and anti-H7 antibodies (Mast Diagnostics, Bootle, UK) diluted 1:250 in PBS for 1 hour at room temperature. After washing three times in PBS, the tissue explants are incubated for 1 hour with secondary anti-rabbit IgG FITC conjugated antibody. The tissue explants are stained with 1 µg/ml Phalloidin-TRITC (Sigma-Aldrich Company Ltd.) washed in PBS and mounted on glass slides using Fluoromount fluorescent mounting medium (Dako Cytomation, Ely, Cambridgeshire, UK). The tissue explants are microscopically examined as whole tissue mounts using a Leica TCS NT confocal system (×63 objective) (Leica Microsystems, GmbH, Heidelberg, Germany).

At 8 hours post-infection, the majority of wild type ZAP 734 form large and compact microcolonies without flagella present, while a minority of bacteria express flagella and are present as single cells. In contrast, ZAP 735 (fliC-) exhibit sparse binding and only occasional microcolonies.

Example 3

Flagella Antiserum Inhibits E. Coli O157:H7 Binding to Bovine Primary Rectal Epithelial Cell To confirm the role of H7 in adherence, inhibition assays are conducted. Overnight cultures of the bacterial strains ZAP 734 and ZAP 735 grown in Mimimal Essential Medium Eagle with Earle's Salts and 25 mM HEPES (M7278, Sigma-Aldrich Company Ltd.) are diluted 1:10 and further grown to an optical density of 0.3-0.4 at $OD_{600}$ in a shaking incubator at 200 rpm at 37° C. for approximately 3 hours. Wild-type ZAP 734 and the isogenic fliC mutant ZAP 735 are treated with rabbit anti-H7 polyclonal antibody (Mast Diagnostics) (using 1:10 dilution in PBS) for 30 minutes at room temperature prior to infection of cells.

The confluent bovine rectal primary epithelial cells grown to confluency as described above, are washed twice in pre-warmed MEM-HEPES (M7278, Sigma-Aldrich Company Ltd.). The bovine rectal primary epithelial cells are infected with the bacteria treated with rabbit anti-H7 polyclonal antibody (Mast Diagnostics) at a multiplicity of infection (MOI) of 1:100 in MEM-HEPES at 37° C., 5% $CO_2$ for 1 hour. The infected cells are washed three times with PBS to remove the non-adherent bacteria. Adherent bacteria are solublised/removed by washing with PBS-0.1% (v/v) Triton X-100 at room temperature, serially diluted, and plated onto LB agar to determine the number of bacteria adhering to the cells in culture as colony forming units (cfu).

In the mutant groups, the addition of antibody has no effect on the mean adherence (p=0.89). However, in the wild type groups the addition of antibody is associated with a statistically significant decrease in adherence (p<0.001). Anti-H7 antibodies reduced the mean number of adherent bacteria from $2.71 \times 10^6$ to $8.21 \times 10^5$ for ZAP 734. For ZAP 735 the cfu remains at $1.6 \times 10^5$. This experiment demonstrates that passive immunity, administering anti-H7 antibodies to an animal, will reduce colonization in and shedding of EHEC from the animal. The antibodies will prevent or reduce binding of EHEC to the animal's intestine.

Example 4

Expression of Flagella by Different EHEC Strains

To test if induction of flagella on contact with the bovine rectal epithelial cells is a general attribute to all the EHEC strains, adherence assays are conducted with EHEC O26:H11 (ZAP 116) and EHEC O113:H21 (ZAP 244) on bovine rectal primary epithelial cells and with two wild-type EHEC strains (ZAP 193 and ZAP 196) on bovine rectal primary epithelial cells as controls. The expression of flagella is examined by immunofluorescence microscopy at 1 hour and 3 hours after infection. The bacteria and bovine rectal primary epithelial cells are cultured as described above. The bovine rectal primary epithelial cells are infected with the bacteria as described above. At 1 hour and 3 hour post-infection, the bovine rectal primary epithelial cells are washed and tagged with rabbit antibodies that are specific for each O-type, as described above. Under immunofluorescence microscopy, both ZAP 193 and ZAP 196 strains express flagella at 1 hour and form compact microcolonies at 3 hours. Bacteria in microcolonies did not express flagella. ZAP 116 (O26:H11) and ZAP 244 (O113:H21) adhere poorly to bovine rectal primary epithelial cells compared to ZAP 196 and ZAP 193 and immunofluorescence microscopy with flagella-specific antibodies shows that these strains do not express flagella at either time point examined.

Example 5

Flagella Possess Adhesive Properties

The adhesive properties of flagella of *E. coli* O157:H7 are examined. To examine flagella adhesive properties, flagella serotypes H7, H11 and H21 from O157, O26, and O113 EHEC strains respectively are purified as follows:

Overnight cultures of ZAP 734 (O157:H7), ZAP 116 (O26: H11) and ZAP 244 (O113:H21) are grown without shaking at 37° C. in 200 ml of LB broth. A 2 ml aliquot of overnight cultures is used to inoculate LB agar plates to grow confluent bacterial lawns overnight. The bacterial lawns are gently suspended in formyl saline (0.4% formalin v/v) (Fisher Scientific UK Ltd., Loughborough, UK). The flagella are mechanically sheared by homogenization on ice (speed 3, 3 minutes) with a "whirling" type blender (Power Gen 125, Fisher Scientific, UK Ltd.). Bacteria are removed by centrifugation (10,000×g, 4° C., 30 minutes) and separating the pellet (bacteria) from the supernatant. The supernatant containing partially purified flagella is further purified by ultracentrifugation (100,000×g, 4° C., 90 minutes) in a swinging bucket rotor centrifuge (model SW-40, Beckman, Durate, Calif.). The pellet is suspended in approximately 11 ml of caesium chloride solution (1.3 g/cm³ density) and is centrifuged at 100,000×g, 4° C., 21 hours in a swinging bucket rotor centrifuge. Flagella form an opaque band at a refractive index of 1.3630 that is collected with a 26-gauge needle into a 1 ml syringe. The purified flagella are resuspended in approximately 11 ml of PBS and pelleted by ultracentrifugation (100,000×g, 4° C., 90 minutes) to remove the caesium chloride. The purified flagella pellet is resuspended in sterilized distilled water and aliquots are kept at −20° C. A mock flagella preparation is prepared in an identical manner using ZAP 735 (fliC mutant) as a control.

Protein concentrations for each flagella preparation is determined using DC Protein Assay kit (Bio-Rad, Richmond, Calif.), using bovine serum albumin as a standard. Bovine serum albumin at a concentration of 2.0 mg/ml is used to make two fold serial dilutions for a standard curve. An aliquot of 10 µl of each isolated flagella types (H7, H11 and H21) are dissolved in 200 µl of distilled water. A 500 µl of Reagent A is added to 100 µl of standard and samples in clean and dry test tubes and vortexed. A further 4.0 ml of Reagent B is added to each tube, vortexed and incubated at room temperature for 15 minutes before reading the absorbance at 750 nm using the spectrophotometer (Genesys 20, Thermo Spectron, Holbrook, N.Y., USA). The concentrations for each flagella sample are calculated from the standard curve for H7 (0.64 mg/ml), H11 (1.1 mg/ml) and H21 (0.35 mg/ml).

To confirm purity, the flagella preparations are adjusted to the same protein concentration and are subjected to sodium dodecyl sulphate polyacrylamide gel electrophoresis (SDS-PAGE). One gel is stained with colloidal blue for visualization. A second gel is transblotted to Immobilon-P membranes (Millipore Corp., Bedford, Mass.). The membrane is blocked overnight with blocking buffer (PBS-Tween 20 (0.1%)-BSA 3%) (Sigma-Aldrich Company Ltd.) at 4° C. and is washed twice with PBS-Tween 20 (0.1%). The membrane is then reacted with rabbit polyclonal antisera specific to each flagellin type (H7, H11 or H21) (Mast Diagnostics) diluted 1:1,000 in blocking buffer for 2 hour at room temperature. Afterwards, the membrane is washed for 2 hours with PBS-Tween 20 (0.1% v/v) at room temperature. The membrane is then incubation with horseradish peroxidase-conjugated goat anti-rabbit IgG (Dalco Cytomation, Ely, Cambridgeshire, UK) diluted 1:3,000 in blocking buffer for 1 hour at room temperature. Bound anti-flagella antibodies are developed in enhanced chemiluminescence reagent (Amersham Pharmacia Biotech, Arlington Heights, Ill.) for visualization.

In the SDS-PAGE stained with colloidal blue and with immunofluorescence, the flagella preparations have three bands for H11 of approximate molecular sizes 50, 90 and 110 kDa, and three bands for H21 of approximate molecular sizes 55, 90 and 110 kDa, and a single band of approximately 66 kDa for H7.

To determine whether these were contaminants or flagella isoforms, samples of each of the 3 main protein bands from each flagella preparation are analysed by MALDI mass spectrometry. After SDS-PAGE, each band is excised from each gel. The proteins are destained and reductively alkylated by adding 50 µl of 10 mM DTT in 100 mM $NH_4HCO_3$ to samples then incubating at 56° C. for 1 hour. Supernatant is removed then 50 µl of 50 mM iodoacetamide in 100 mM $NH_4HCO_3$ followed by incubation at room temperature in the dark for 30 minutes. Supernatant is removed then gel pieces are washed with 300 µl of 100 mM $NH_4HCO_3$ for 15 minutes. After removal of supernatant, the gel pieces are washed with 300 µl of 20 mM $NH_4HCO_3$/acetonitrile (50:50 v/v) for 15 minutes then supernatant is removed. Gel pieces are dried in a DNA 120 SPEEDVAC™ concentrator (Thermo Spectron, Holbrook, N.Y., USA) for 30 minutes then subjected to trypsinization. Dried gel pieces are transferred into a 500 µl microcentrifuge tube, 400 µl of 50% acetonitrile in 25 mM $NH_4HCO_3$ buffer pH 8.0 is added and left for 15 minutes after which supernatant is removed. Gels are washed twice more with 400 µl aliquots with the same solution then soaked in 100% acetonitrile for 5 minutes. Acetonitrile is then removed, and the gel slices dried for 20-30 minutes in a DNA 120 SPEEDVAC™ concentrator (Thermo Spectron, Holbrook, N.Y., USA). Gels are rehydrated with a minimal volume of Trypsin solution (10 µg/ml in 25 mM $NH_4HCO_3$ buffer pH 8.0) and incubated at 37° C. for 16-24 hours. After digestion trypsin solution, if any, is removed into duplicate 500 µl microcentrifuge tubes. 25-50 µl of 50% acetonitrile/5.0% trifluoroacetic acid is then added to the remaining gel and left to soak for 30-60 minutes after which it is aspirated and transferred to the corresponding duplicate tube, combining it with the trypsin solution. Gels are then re-extracted with another 25-50 µl aliquot of 50% acetonitrile/5.0% trifluoroacetic acid and combined with previous extracts. Extracts are dried in a DNA 120 SPEEDVAC™ concentrator (Thermo Spectron) until completely dry then stored at −20° C. until analysis mass spectrometry.

Dried samples are reconstituted by adding 3 µl of 50% acetonitrile/0.1% trifluoroacetic acid to until the extracted peptides are dissolved. Reconstituted samples (0.5 µl) are mixed with an equal volume of matrix (a saturated solution of α-cyano-4-hydroxycinnamic acid in 100% acetonitrile/0.1% trifluoroacetic acid) on a MALDI sample plate. After the spots have dried completely, the plates are loaded into the mass spectrometer for acquisition of ion spectra using a Voyager DE-PRO MALDI-ToF mass spectrometer (Applied Biosystems, Foster City), scanning the 600 to 5000 dalton region in reflectron mode producing monoisotopic resolution. The spectra generated are mass calibrated using known standards, and the peaks are deisotoped. Masses obtained are then database searched using the MASCOT search engine and the NCBInr and Swissprot databases. Searches are conducted using 50 ppm and 100 ppm mass tolerance windows. All bands in each of the preparations are confirmed as FliC of the appropriate serotype.

The purified flagella from the different EHEC serotypes are incubated with bovine rectal primary epithelial cells. The bovine rectal primary epithelial cells are cultured as described above. The cells are washed 3× with pre-warmed MEM-HEPES and incubated with isolated flagella 5 µg/ml (H7, H11 or H21) for 3 hours at 37° C., 5% $CO_2$. The cells are washed 3 times in PBS to remove loosely associated flagella. The cells are fixed and permeabilized with 2% (V/V) formalin/0.2% (v/v) Triton X-100. Primary rabbit flagellar H-type specific antibodies (Mast Diagnostics) diluted 1:250 in PBS are added for 1 hour at room temperature. After washing, the cells are incubated for 1 hour with secondary anti-rabbit IgG FITC/TRITC-conjugated antibodies (Sigma-Aldrich Company Ltd.) diluted 1:1000 in PBS at room temperature. The cells are stained with TRITC-phalloidin (1 µg/ml) (Sigma-Aldrich Company Ltd.) and TO-PRO (Molecular Probes) for 20 minutes each at room temperature. The cells are washed extensively with PBS, mounted in Fluoromount fluorescence mounting medium (Dako Cytomation) and examined using a Leica TCS NT confocal microscope. The H7, but not the H11 and H21 flagella, bind to the bovine rectal epithelial cells.

Example 6

Purified H7 Flagella Inhibits *E. Coli* O157:H7 Binding to Bovine Rectal Primary Epithelial Cells To further demonstrate that H7 acts as an adhesin, the bovine rectal primary epithelial cells, cultured as described above, are pre-incubated with purified H7 flagella (0.025 µg/ml to 2.0 µg/ml for 3 hours in MEM-HEPES (Sigma-Aldrich Company Ltd.) at 37° C., 5% $CO_2$, 95% air in a humidified atmosphere for 30 minutes before the addition of bacteria at MOI of 1:100. After pre-treatment of cells with purified flagella, adhesion of *E. coli* O157:H7 decreases in a dose-dependent manner. A comparison of the mean cfu at the 0.25 µg/ml dose with that of negative control shows that this dose of flagellin is associated with a statistically significant drop in the mean numbers of adhering bacteria (p=0.02). Mean number of adhering bacteria at different concentrations of H7 added are: $2.4 \times 10^4$ (control), $2.1 \times 10^4$ (0.025 µg/ml), $1.8 \times 10^4$ (0.25 µg/ml), $2.08 \times 10^4$ (0.5 µg/ml), $1.9 \times 10^4$ (1.0 µg/ml), $2.21 \times 10^4$ (2.0 µg/ml), $7.4 \times 10^4$ (4.0 µg/ml). Surprisingly, at 4.0 µg/ml H7 flagella significantly enhances the *E. coli* O157 binding. This pattern was repeated on two replicate assays.

Example 7

Vaccination of Calves with Purified H7

The aim of this trial is to evaluate the effect of immunisation with purified H7 antigen (purified using the procedures set forth above) on subsequent colonisation of *E. coli* O157:H7 in cattle. The experimental outline is shown in Table 3 below. Eight to nine week old naïve calves are immunised on three separate occasions at two week intervals with either 60 µg purified H7 by intra-muscular injection (with 5 mg Quil A as an adjuvant), 60 µg purified H7 per rectum (no adjuvant), or 60 µg purified H7 encapsulated into poly(D,L-lactide-co-glycolide) microspheres (PLG:H7) per rectum. A control group received no vaccinations. Ten days after the final immunisation, calves are challenged orally with $10^{10}$ cfu of *E. coli* O157:H7 strain Walla $3^{nalR}$, and colonisation is assessed by serial analysis of faecal bacterial counts.

TABLE 3

| Group number | n | Immunisation protocol |
| --- | --- | --- |
| 1 | 8 | 60 µg H7 + 5 mg Quil A by intra-muscular injection |
| 2 | 8 | 60 µg H7 per rectum |
| 3 | 8 | 60 µg PLG:H7 per rectum |
| 4 | 8 | Non-vaccinated control |

To evaluate specific antibody responses to H7 after vaccination, serial serum, nasal swab and rectal swab samples are subjected to ELISA to detect both anti-H7 IgA and anti-H7 IgG antibodies. High levels of both serum anti-H7 IgG and IgA are induced following intra-muscular injection of H7 (titres>10,000 for IgG and >1,000 for IgA). However, per rectal immunisation with H7 induces only low levels of serum anti-H7 antibodies, and per rectal immunisation with PLG: H7 fails to induce any serum antibody response to H7. Both anti-H7 IgG and IgA antibodies are detected in nasal and rectal swab samples following intra-muscular injection of H7. Anti-H7 IgA (but not IgG) antibodies are detected in rectal swab samples following per rectal immunisation with H7, but neither IgG nor IgA were detected following per rectal immunisation with PLG:H7. Nasal swab samples following per rectal immunisation with H7 and per rectal immunisation with PLG:H7 did not contain detectable levels of anti-H7 IgG or IgA.

To evaluate the faecal shedding of E. coli O157:H7 after immunization with purified H7, the area under the shedding curve (AUC) is calculated for each calf between days 3 and 14 post challenge. The variation in AUC within groups was not normally distributed so analysis is performed by calculating the uptake rate, the proportion of individuals within a group successfully colonised by E. coli O157:H7, and then subjected to Fisher's exact test.

It was therefore necessary to define successful colonisation, which was achieved by calculating AUC within the 3 to 7 day and 7 to 14 day post-challenge periods for groups 1 and 4. By plotting a graph of $AUC_{3-7}$ against the $AUC_{7-14}$ it was possible to define a distinct population with $AUC_{3-7}<10$ and $AUC_{7-14}<10$ that were not colonised. Based on this definition of successful colonisation, uptake rates were calculated and compared using Fisher's exact test.

The uptake rates can be compared between groups using Fisher's exact test on a 2×2 matrix (see Table 4). Comparison of groups 1 and 4 does not yield a significant difference due to the limited number of animals, however, including groups 2 and 3 as additional unvaccinated control animals (see below*), reduces the P-value to well below the 5% level of significance (0.002).

TABLE 4

Uptake rates, Fisher's exact test (2 × 2)

| Uptake | Group 1 | Group 4 | 1 vs 4 | Groups 2, 3 & 4 | 1 vs 2, 3 & 4 |
|---|---|---|---|---|---|
| Successful | 3 | 6 | | 22 | |
| Failed | 5 | 2 | | 2 | |
| Uptake Rate | 0.375 | 0.75 | | 0.92 | |
| Mid P-value | | | 0.089 | | 0.002 |

A more sophisticated version of Fisher's exact test using larger matrices, in this case a 4×2, is performed (see Table 5). This test yields a P-value of 0.006. This P-value is the probability of observing this result with the null hypothesis that there are no differences in the colonisation susceptibility of calves between groups. *These analyses have the caveat that Groups 2 and 3 (mucosal vaccinated groups) are included on the assumption that there is no biological reason for them having a higher rate of uptake than the other groups. For example, it is possible that the mucosally applied H7 antigen induces immune tolerance which reduces the normal response to bacterial challenge. This possible tolerance can be discounted on the basis that the H7 antibody responses to bacterial challenge in both serum and mucosa are similar in the unvaccinated control and mucosally vaccinated groups.

TABLE 5

Uptake rates, Fisher's exact test (4 × 2)

| Uptake | Group 1 | Group 2 | Group 3 | Group 4 |
|---|---|---|---|---|
| Successful | 3 | 8 | 8 | 6 |
| Failed | 5 | 0 | 0 | 2 |
| Uptake Rate | 0.375 | 1.0 | 1.0 | 0.75 |
| Group Mean AUC | 18.13 | 36.84 | 38.24 | 31.34 |
| Mid P-value | | 0.006398 | | |

The unvaccinated group contains 2 calves that do not become colonised following the first challenge which would be considered a normal outcome based on previous experience with this model. The poor uptake of the intra-muscular vaccinated group is less than would normally be expected with this model, especially considering the good uptake rate of the other groups with the same bacterial inoculum. This poor uptake may be a consequence of the anti-H7 antibody responses to vaccination, detected in this group. Of the other groups only the per rectal H7 group exhibited an antibody response and this differed from the intramuscular vaccinated group in that IgG antibodies were not detected in the rectal swabs and neither IgG nor IgA were detected in the sera and nasal swabs. It is therefore possible to conclude that there is a statistically significant effect of intra-muscular vaccination with H7 to inhibit experimental colonisation of the challenge strain.

It is noted that three of the calves in group 1 are colonised by the challenge strain, including one calf that shed relatively high levels for a relatively long period. The antibody responses of these calves are not quantitatively different from the group 1 calves that are not colonised. It is possible that H7 specific mucosal antibodies are preventing colonisation by immune exclusion, i.e. they bind to flagella expressing bacteria and prevent non-specific functions and/or interactions with the host epithelium. If so, then bacteria not expressing flagellae (expression of which is known to be phase variable) could have a selection advantage over those bacteria that are. Thus aflagellate bacteria are free to establish mucosal colonisation although there is a reduced probability of uptake because a lower proportion of the total challenge inoculum is capable of establishing mucosal colonisation. This explanation requires that flagellae themselves are not the sole adherence/colonisation factors. Flagellae have been demonstrated not to be essential for E. coli O157:H7 colonisation of the rectal mucosa of experimentally challenged calves by gene knock out studies (Dobbin H S, et al.; The Escherichia coli O157 flagellar regulatory gene flhC and not the flagellin gene fliC impacts colonization of cattle, Infect. & Immun., 74(5): 2894-905 (May 2006)) and other bacterial factors (such as intimin and the LEE type III secretion system) are known to contribute to attachment and persistence. Although flagellae are not essential for colonisation by E. coli O157:H7, the data presented here indicate that H7 flagellae play a significant role in adherence to bovine rectal epithelium (Examples 1, 2, 3, 5 & 6). Combined with the suggestion that anti-H7 antibodies reduce the probability of initial colonisation in calves, H7 is an important protective antigen.

Example 8

Production of Recombinant H7

Purified chromosomal DNA from E. coli O157:H7 (EDL933) is amplified using primers: forward primer: CCGGATCCTCTGCGCTGTCGAGTTCTATCG (SEQ ID NO: 3) and reverse primer: CCAAGCTTTTAACCCTGCAGCAGAGAC (SEQ ID NO:4). PCR amplification occurs with an annealing temperature of 58° C. (2 minute extensions) and creates a 1746 base pair product that is then cleaved sequentially with BamHI and HindIII and ligated with pET41a (+) (Novagen) restriction digested with the same enzymes. The resulting clone is then transformed into E. coli BL21 (DE3) (Novagen). Expression of the recombinant H7 protein is carried out in LB medium induced with 1 mM IPTG for 4 hours so that the culture reaches an optical density (600 nm) of 0.5. The bacteria are then harvested by centrifugation and suspended in sonication buffer (10 mM NaCl, 50 mM Tris-HCl (pH7.6), 1 mM EDTA and 0.1 mM dithiothreitol) containing protease inhibitors. One can purify the recombinant protein using either the GST moiety or the histidine tag included in the recombinant protein. For purification, one uses commercial resins/columns and follows manufacturers guidelines. The GST/6× His tags ("6× His" disclosed as SEQ ID NO: 6) can be removed by treatment of the recombinant protein with enterokinase.

Example 9

Vaccination with Recombinant H7 Flagella Reduces EHEC O157:H7 Shedding from Bovine Purified, recombinant H7 is mixed with a water-in-oil-in-water adjuvant. The mixture is injected into cattle i.m. The dose can range from approximately 2 ml to approximately 10 ml, preferably approximately 2 ml to approximately 5 ml. The amount of H7 in each dose can range from approximately 1 µg to approximately 100 mg. While one dosage is sufficient, one can also provide one or more boosters approximately 2 weeks to approximately 26 weeks later. While it is preferable to administer the injection to naïve calves, one can also treat cattle that have already been exposed to *E. coli* O157:H7.

In one preferred embodiment, cattle are immunized intramuscularly on three occasions at intervals of 14 days with about 50 mg to about 100 mg recombinant or purified H7 protein combined with a suitable adjuvant such as Quil A (5 mg). Blood and mucosal samples from before and after immunization (days-4, 7, 21 and 35) are taken to monitor induction of antibody responses by H7 antigen-specific ELISA.

Efficacy is established following oral challenge with approximately $10^9$-$10^{10}$ cfu of *E. coli* O157:H7 strain Walla Walla 3 on day 39. Feces are sampled at least three times a week for three weeks after challenge to determine levels of bacterial shedding. Blood and mucosal samples are also taken to monitor antibody responses following bacterial challenge.

In addition, a different group of cattle are immunized per rectum on three occasions at intervals of 14 days with about 50 mg to about 100 mg recombinant H7 or recombinant H7 incorporated into microparticulate carrier such as PLG. Blood levels and challenge are the same as the intramuscular injection groups. Blood and mucosal samples are also taken to monitor antibody responses following bacterial challenge.

Example 10

Systemic Immunization of Ruminants

Figure 1:
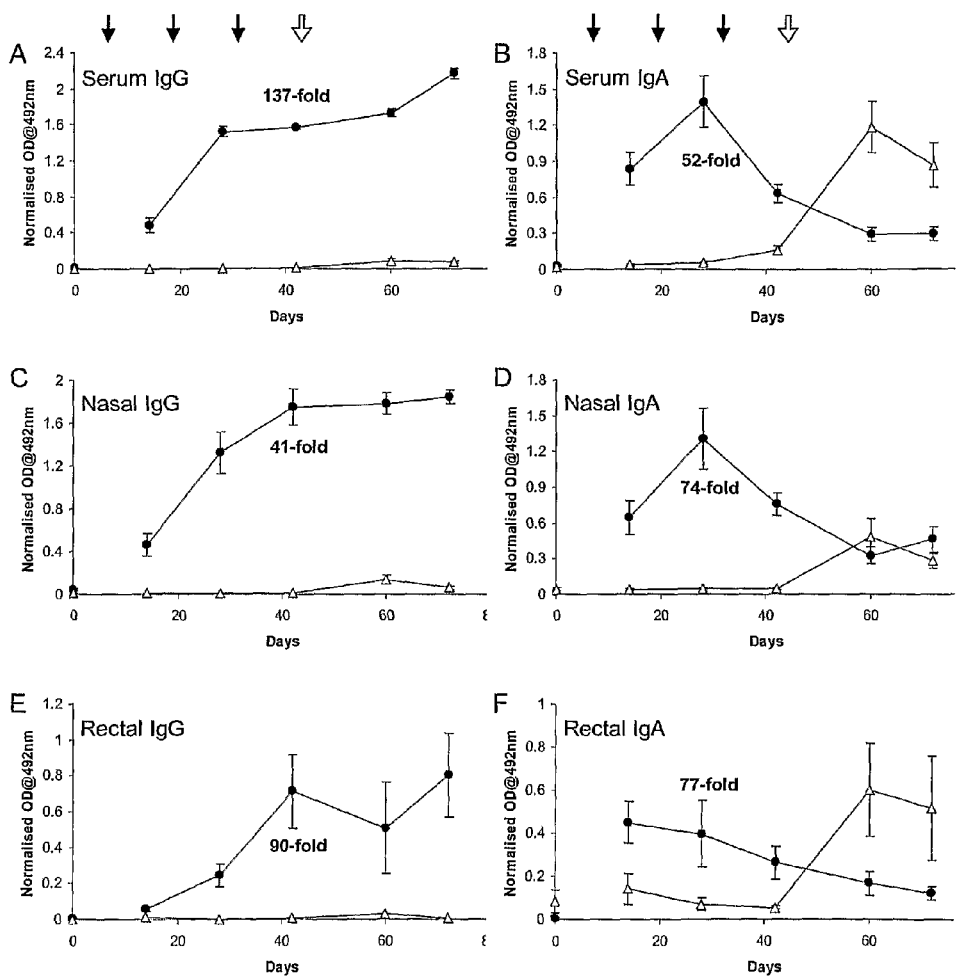

Systemic (intra-muscular, IM) immunization of ruminants (cattle and sheep) with the bacterial flagellin H7 in combination with Quil A adjuvant has been shown to result in a mucosal IgA antibody response to H7 (FIGS. 1 and 4 A and B; (McNeilly et al., (2008) Infect. Immun. 76: 2594-602). Furthermore, when cattle are systemically immunised with EspA fused to the C-terminus of H7 flagellin in combination with Quil A, a mucosal response is induced and anti-EspA IgA antibodies (see FIG. 8A). In contrast, the systemic immunization of cattle with EspA, together with but not fused to H7 flagellin, and in combination with Quil A, does not result in any mucosal anti-EspA IgA response (see FIG. 8C).

Example 11

TLR5 Activity

TLR5 activation appears to be critical for the systemic induction of a mucosal IgA response to both H7 and any fused antigen. By way of example, when the C-terminus of H7 is fused to the *Teladorsagia ciretinzcincta* nematode antigen Tc-SAA, TLR5 activity is abrogated. and IM immunization of this fusion protein does not result in any mucosal IgA response to either H7 or Tc-SAA (see FIGS. 9 A and B). In contrast, IM immunization with either native or recombinant H7, both of which activate TLR5, results in a mucosal anti-H7 IgA response (see FIGS. 9 A and B). The ability of the H7 antigens used in this study to activate TLR5 was assessed using an in vitro bioassay based on TLR5 dependant IL-8 release from Caco-2 cells (see FIG. 9 C).

Example 12

TLR5 Activating Fusions

H7 flagellin has been sequenced (nucleotide sequence SEQ ID NO: 1 (FIG. 5A); amino acid sequence SEQ ID NO: 2 (FIG. 5B)) and consists of a central variable region specific to H7 flagellin and conserved domains at the N and C termini. Toll-like receptor 5 (TRL5) binding domains are present within these conserved N and C terminal domains. Ligation of TLR5 is the principle mechanism by which bacterial flagellins modulate immune responses (Hayashi et al., (2001) Nature 410: 1099-1103).

Accordingly, H7 flagellin fusion proteins can be generated which retain TLR5 signaling activity by either fusion of antigen to the N-terminus or C-terminus of H7 flagellin or insertion of antigens into the central variable region of H7 flagellin as illustrated in FIG. 6. Insertion of antigens into the variable D3 region of H7 is possible using the internal Acc-1 restriction sites identified in FIGS. 5A and B.

By way of example, H7 flagellin fusions of the *E. coli* O157:H7 protein EspA fused to either the C-terminus of H7 or inserted into the central variable region of H7 have been constructed and have been shown to be capable of TLR5 activation (see FIGS. 7 A and B). E2, the major envelope protein of Bovine Viral Diarrhoea Virus has also been fused to the C-terminus of H7 flagellin and is capable of TLR5 activation (FIG. 7A).

While this invention has been described with a reference to specific embodiments, it will be obvious to those of ordinary skill in the art that variations in these methods and compositions may be used and that it is intended that the invention may be practiced otherwise than as specifically described herein. Accordingly this invention includes all modifications encompassed within the spirit and scope of the invention as defined by the claims.

Further examples:
Materials and Methods
Purification of *E. coli* O157:H7 Flagellin Flagellin (H7) was isolated from *E. coli* O157:H7 (stx-) strain ZAP984, a LEE4 deletion mutant derived from strain ZAP 198 by acid dissociation, neutral pH re-association and ammonium sulfate precipitation. Purity was verified using polyacrylamide gel electrophoresis (PAGE) followed by Simply Blue staining (Invitrogen, San Diego, Calif.), and by western blotting.

Western Blotting

Samples of H7 flagellin were separated by PAGE using NUPAGE® 4-12% Bis-Tris gels (Invitrogen) under reducing conditions, and transferred to nitrocellulose membranes (pore size 0.2 µm) using the XCELL II™ blotting system (Invitrogen) according to the manufacturer's instructions. Membranes were subsequently washed in PBS containing 0.5M NaCl and 0.5% (v/v) Tween 80 (PBS/NaCl/T80) for 1 hr at RT. Blots were incubated for 1 hour at RT with rabbit polyclonal anti-H7 antibody (MAST-ASSURE™, Bootle, UK) diluted 1:500 in PBS/NaCl/T80, followed by incubation for 1 hour at RT with a 1:2000 dilution of goat anti-rabbit polyclonal antibody conjugated to HRP (Dakocytomation, Ely, UK). Controls included omission of the primary antibody, and substitution of primary antibody with normal rabbit serum. HRP was detected after final washing by incubating blots with ECL Plus reagent (GE healthcare, Little Chalfont, UK).

Immunisation Protocol and Oral Bacterial Challenge

Immunisations and oral bacterial challenges were performed at Moredun Research Institute (MRI) under Home Office license 60/3179. Ethical approval was obtained from the MRI Animal Experiments Committee. Two groups of 8 conventionally reared male Holstein-Friesian calves were immunised on 3 separate occasions at 2 weekly intervals as follows: group 1 received 60 mg H7 flagellin+5 mg Quil A (Brenntag Biosector, Frederikssund, Denmark) in 2 ml PBS intra-muscularly (i.m); group 4 received no immunisations (non-vaccinated control (NVC) group). The average age of calves at the time of the first immunisation was 9±2 weeks, and faecal samples obtained from each calf prior to immunisation were confirmed to be negative for $E.\ coli$ O157:H7 by immunomagnetic separation, performed according to the manufacturer's instructions (DYNABEADS® anti-$E.\ coli$ O157, Invitrogen).

Ten days after the last immunisation, calves were orally challenged with $10^{10}$ CFU naldixic acid-resistant $E.\ coli$ O157:H7 (stx-) strain ZAP198 and viable $E.\ coli$ O157:H7 bacteria per gram of surface faeces (CFU/g faeces) were enumerated daily post-challenge by plating onto sorbitol MacConkey agar plates containing 15 µg/ml naldixic acid (Oxoid) as previously described. To estimate total bacterial faecal shedding, daily bacterial counts were plotted vs. time for each calf and the area under shedding the curve (AUC) was calculated. In addition, bacterial uptake rates (as defined by an increasing faecal bacterial count from 3 days post-challenge) were recorded. Serum, nasal secretions and rectal swabs were collected as described previously 4 days prior to first immunisation, 1 week after each immunisation, and 2 weeks after oral bacterial challenge. Calves were euthanased 3 weeks after bacterial challenge, and abomasal and small intestinal swabs were collected in addition to serum, nasal secretions and rectal swabs.

Quantification of Anti-H7 Flagellin and Anti-O157 LPS Antibodies

H7 flagellin-specific IgA and IgG antibodies were quantified in serum, nasal secretions and intestinal swab samples by indirect ELISA. Samples were diluted 1:1000, 1:10 and 1:2.5 for serum, nasal secretions and intestinal swab samples respectively following serial dilution of representatives from each to ensure that the colour reaction product at $OD_{492}$ (optical density at 492 nm) for the samples was on the linear part of the curve. ODs obtained for intestinal swab samples were normalised to total IgA, measured using a sandwich ELISA obtained from Bethyl Laboratories Inc. (Montgomery, Tex.), and inter-plate variation was normalised to a positive control. Western blotting was also performed on selected pre-immunisation, post-immunisation or post-bacterial challenge samples of serum, nasal secretions and rectal swab samples from each immunisation group to confirm the specificity of the antibody responses measured by ELISA (data not shown).

Statistical Analysis

All statistical analyses were performed using the statistical package Genstat, 7th edition. ELISA and bacterial shedding data were $\log_{10}$ transformed before analysis to ensure that observations within each group had an approximately normal distribution with a common variance. ELISA data from the different immunisation groups 1 week after the final immunisation and at post-mortem (for abomasal and small intestinal swabs only) were compared using one-way ANOVA. Differences between post-immunisation and post-bacterial challenge ELISA data within each immunisation group were compared using a paired t-test. Daily means of faecal bacterial shedding data were analysed as repeated measures using REML with estimates of missing values. Standard error of the differences were calculated and used to compare group mean bacterial shedding at each time-point using a one-tailed t-test. AUC data from different immunisation groups were compared by ANOVA, and uptake rates between groups were compared using Fisher's exact test using a 2×2 matrix. All ANOVA was followed by the Tukey post hoc test for pairwise comparison of means.

Results

H7 Specific Antibody Responses Following Immunization with H7 Flagellin and Subsequent Oral Bacterial Challenge Serum, nasal and rectal H7-specific antibody responses are shown in FIG. 1. High titres of anti-H7 IgG and IgA were induced in both serum and nasal secretions following i.m. injection of H7, and IgG and IgA antibody levels were maximal after the third and second immunisation respectively (FIGS. 1A-D).

Anti-H7 IgG and IgA antibodies were detected in rectal swab samples following i.m. immunisation with H7 (FIG. 1E).

Specificity of the Response to H7 Flagellin

Figure 2:
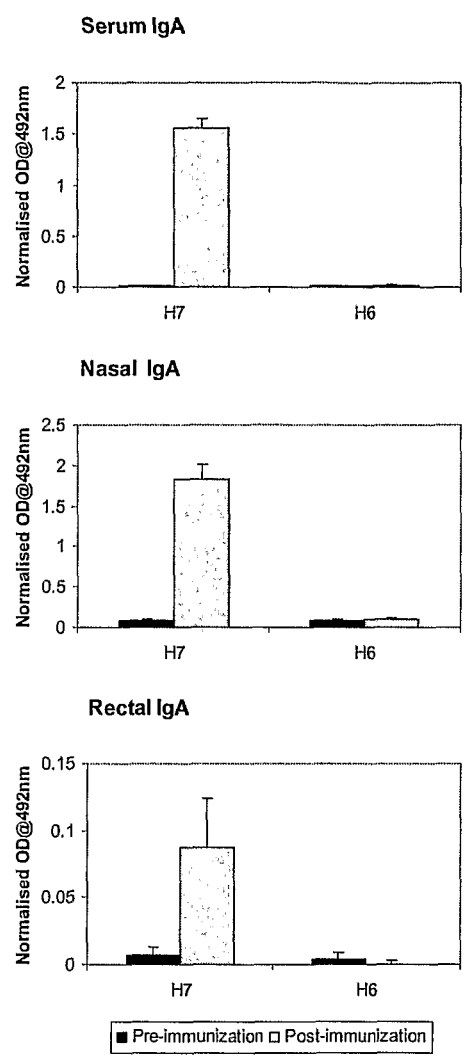
FIG. 2 shows specificity of the IgA response for H7 rather than H6 flagellin following IM immunisation with purified H7 flagellin.

The IgA response in serum, nasal secretions and rectal swabs following IM H7 immunisation was specific for H7 and not H6. Post-immunisation samples were analysed after the second immunisation i.e. at peak IgA levels (FIG. 2). This indicates that it is much more likely that the mucosal response generated following IM immunisation with H7 is an inherent property of H7 rather than due to cross-priming with other flagellins.

$E.\ coli$ O157:H7 Colonisation Following Immunization with H7 Flagellin

Figure 3:
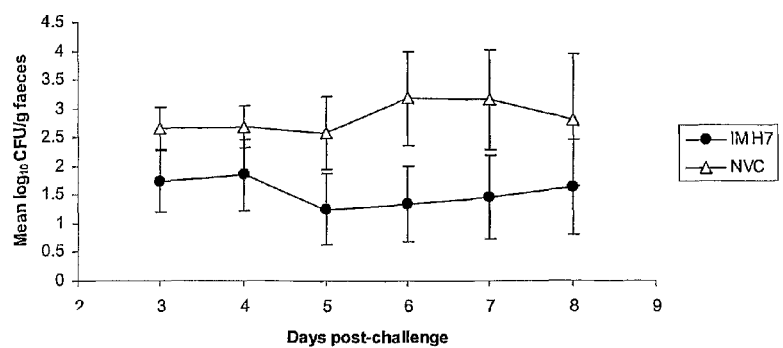
FIG. 3 shows faecal shedding of E. coli O157:H7 following oral challenge of calves previously vaccinated systemically with H7 flagellin.

Following immunisation, oral bacterial challenge with $E.\ coli$ O157:H7 resulted in successful colonization of 3/8 calves in the i.m. immunized group compared to 100% of rectally immunized and 6/8 non-vaccinated calves. Daily mean bacterial counts calculated for both colonized and non-colonised calves are shown in FIG. 3. Overall, for the 21 day shedding period analysed there was a treatment (immunisation)×time interaction (P=0.009) that was reflected in lower mean bacterial counts in the i.m. immunized group compared to rectally immunized and control groups on days 5 to 8 post-challenge (P<0.05).

Discussion

Many infectious agents enter the body at mucosal surfaces and therefore mucosal immune responses are important for protection against disease. Most vaccines in use today are delivered systemically by intra-muscular (i.m.) or subcutaneous injection (sc). Systemic immunisations with antigen, while practically easy to administer, generally induce a systemic and not a mucosal immune response. In contrast, vaccines delivered onto mucosal surfaces are more effective at inducing mucosal immune responses but have major practical limitations including difficulty of administration, antigen degradation and poor antigen uptake. A solution to this problem would be to develop immuno-modulators within vaccines, which could direct immune responses generated by systemic immunisation to the mucosa.

A key finding of this study is that an H7-specific mucosal IgA response was induced in both nasal secretions and rectal swab samples following i.m. immunisation of cattle with purified H7. This finding is unusual as systemic routes of immunisation generally result in poor mucosal IgA levels. However, confidence in the result can be gained by the following observations: firstly, previous analyses of the mucosal sampling techniques employed in this study have shown that IgA present in the mucosal samples is locally i.e. mucosally derived. Secondly, analysis of gel filtration fractions of nasal secretions from i.m. immunised calves indicate that the anti-bovine IgA antibodies employed in the H7 ELISA do not appear to cross react with bovine IgG to any great extent (data not shown).

The invention claimed is:

1. A method of generating a mucosal and/or IgA response to a target protein in a subject in need thereof, comprising parenteral administration of an adjuvant and a fusion protein comprising *Escherichia coli* H7 or a Toll-like receptor 5 (TLR5) activating fragment thereof and the target protein, wherein the fusion protein activates TLR5.

2. The method of claim 1, wherein the subject is an agricultural animal.

3. The method of claim 2, wherein the agricultural animal is a ruminant animal.

4. The method of claim 1, wherein the target protein is fused to a terminal portion of the H7 protein or TLR5 activating fragment thereof or inserted into an internal region of the H7 protein.

5. The method of claim 4, wherein the terminal portion is the N- or C-terminus of the H7 protein or TLR5 activating fragment thereof, and the internal region is the variable region of the H7 protein.

6. The method of claim 1, wherein the target protein is a protein which by itself does not or poorly elicits a mucosal and/or IgA response.

7. The method of claim 1, wherein the target protein is selected from intimin, EspA, B and D, efa-1, Iha, outer membrane proteins and porins from *E. coli* or fragments of any of these.

8. The method of claim 1, wherein the target protein is a protein or protein fragment from a pathogenic organism which infects an animal host through adhesion to and/or colonisation of a mucosal surface.

9. The method of claim 8, wherein the pathogenic organism is a bacterium other than *E. coli*, a nematode or a virus.

10. The method of claim 1, wherein the target protein is selected from the major envelope glycoprotein (E2) of Bovine Viral diarrhoea Virus, the F protein of Bovine Respiratory Syncitial Virus (BRSV), the gB and gD glycoproteins of Bovine Herpes Virus-1 (BHV-1), the F and HN proteins of bovine parainflueza-3 (PI-3) virus or fragments of any of these.

11. The method of claim 1, wherein said H7 or TLR5 activating fragment thereof is derived from *Escherichia coli* O157:H7.

12. The method of claim 1, wherein the H7 has an amino acid sequence at least 97% homologous to SEQ ID NO: 1.

13. The method of claim 1, wherein the H7 has the amino acid sequence provided by SEQ ID NO: 1 or is encoded by the nucleic acid sequence provided by SEQ ID NO: 2.

* * * * *